United States Patent [19]

Blanchard

[11] Patent Number: 5,851,810
[45] Date of Patent: Dec. 22, 1998

[54] NUCLEIC ACID ENCODING RHODOCOCCUS PHENYLALANINE DEHYDROGENASE

[75] Inventor: John S. Blanchard, Pelham Manor, N.Y.

[73] Assignee: Albert Einstein College of Medicine of Yeshiva University, a Division of Yeshiva University, Bronx, N.Y.

[21] Appl. No.: 461,990

[22] Filed: Jun. 5, 1995

[51] Int. Cl.[6] .............................. C12N 9/02; C12N 1/20; C12N 15/00; C07H 21/04
[52] U.S. Cl. ................. 435/189; 435/252.3; 435/252.33; 435/320.1; 435/822; 536/23.2
[58] Field of Search ................. 435/69.1, 252.3, 435/252.33, 189, 320.1, 822; 536/23.2

[56] References Cited

U.S. PATENT DOCUMENTS 4,970,157   11/1990   Hibino et al. ............................ 435/189

OTHER PUBLICATIONS

Brunhuber et al. (1993) FASEB J. 7(7), p. A1069, Abstract 98.

Brunhuber et al. (1994) J. Biol. Chem. 269, 16203–16211.

*Primary Examiner*—Rebecca E. Prouty
*Assistant Examiner*—Elizabeth Slobodyansky
*Attorney, Agent, or Firm*—Amster, Rothstein & Ebenstein

[57] ABSTRACT

The present invention provides a purified and isolated nucleic acid encoding Rhodococcus L-phenylalanine dehydrogenase. The present invention also provides a vector comprising nucleic acid encoding Rhodoccus L-phenylalanine dehydrogenase, a host cell transformed with the vector, and a method for producing recombinant L-phenylalanine dehydrogenase.

14 Claims, 8 Drawing Sheets

```
                                                                                   343
244  CTGCAGAGACGTTTTCGCCAAAGACTGGTCACACTATGAAGACGCACCCTCCGTCGCCGGAGACCCGAATCGGGAGTTGTCTGCGTCCACT
         PstI
         "RBS"    BspHI                                                            443
344  GCATCCATCGAACATCAAGGGGTACATCATGAGTATCGACAGCGCACTGAATGACGGTCACCCGATTCGACCGGAGACTGGTGCC
                                   M  S  I  D  S  A  L  N  D  G  E  M  T  V  T  R  F  D  R  E  T  G  A    24
  1

543
444  CATTTCGTCATTCGACTCGATTCGACCCAACTCGGACGGCCGGAGGCACCAGAGCCGCACAGTACTCACAGCTGGCGGACGCCCTCACCGACGCCG
      H  F  V  I  R  L  D  S  T  Q  L  G  P  A  A  G  G  T  R  A  A  Q  Y  S  Q  L  A  D  A  L  T  D  A  G    58
 25

643
544  GCAAATTGGCGGGGCGATGACGTTGAAGATGGCAGTGAGCAACCTTCCGATGGGCGGGGGCAAATCCGTCATTGCGCTTCCTGCCGCGTCATTCGAT
      K  L  A  G  A  M  T  L  K  M  A  V  S  N  L  P  M  G  G  G  K  S  V  I  A  L  P  A  P  R  H  S  I    91
 59

743
644  CGATCCCGAGCACGTGGGCARCATCCTCCGAATCCACGCGATCATGACAAGTTGTCCGGCAACTACTGAGACCGAGACTGTCAACACCAATTCG
      D  P  S  T  W  A  R  I  L  R  I  H  A  E  N  I  D  K  L  S  G  N  Y  W  T  G  P  D  V  N  T  N  S    124
 92

843
744  GCAGACATGGATACTCTGAACGACACCACCGAGTTCGTGTTCGGACGGTCGCTCGAACGGCGGCGGGTTCGAGCGCGTTCACCACCGCCGTTGGCG
      A  D  M  D  T  L  N  D  T  T  E  F  V  F  G  R  S  L  E  R  G  G  A  G  S  S  A  F  T  T  A  V  G    158
125

943
844  TGTTCGAGGCGATGAAGGCGACCGTCGCGCACCGTGGGCTCACTCGACGGTTTGACGGTCCTGGTCCAAGGACTGGGCAGTCGGAGGATCATT
      F  E  A  M  K  A  T  V  A  H  R  G  L  G  S  L  D  G  L  T  V  L  V  Q  G  L  G  A  V  G  G  S  L    191
159
```

FIG. 3A

```
 944  GGCATCCCTGGCCGCCGAAGCGGGTGCGCAACTCCTGGTGCAGAGACACCGAGCGAGTAGGCGACGCTGTTGCGTTGGGCCACACAGCGGTTGCC  1043
 192   A  S  L  A  A  E  A  G  A  Q  L  L  V  A  D  T  D  T  E  R  V  A  H  A  V  A  L  G  H  T  A  V  A   224

1044  CTCGAGGACGTTCTGTCCACCCCGTGTGATGTCTTCGCACCCTGCGCAATGGGCGGCGTCATCACCGAGGTGGCGCGAACACTCGACTGTTCCGTCG  1143
 225   L  E  D  V  L  S  T  P  C  D  V  F  A  P  C  A  M  G  G  V  I  T  T  E  V  A  R  T  L  D  C  S  V  V   258

1144  TGGCCGGTGCCGCCAACAACGTCATCGCCGACGAGGCCGCCTCGGACATCCTGCACGCACGCGGAATTCTGTACGCTCCCGACTTCGTGGCCAACGCCGG  1243
 259   A  G  A  A  N  N  V  I  A  D  E  A  A  S  D  I  L  H  A  R  G  I  L  Y  A  P  D  F  V  A  N  A  G   291

1244  CGGTGCCATCCACCTCGTAGGCCGGGAGGTTCTCGGTTGTCCGAGTCGGTTGTCCACGAACGAGCAGTTGCCATAGGCCGACACCCTGAATCAGGTCTTC  1343
 292   G  A  I  H  L  V  G  R  E  V  L  G  W  S  E  S  V  V  H  E  R  A  V  A  I  G  D  T  L  N  Q  V  F   324

1344  GAGATCTCCGACAACGACGGCGTCACCCCGGACGGCCCGCCACTCTCGCTGGACGGCGCGCCCGAGGCCTCGACAACGACAGCGACTGCCTAGT  1443
 325   E  I  S  D  N  D  G  V  T  P  D  E  A  A  R  T  L  A  G  R  R  A  R  E  A  S  T  T  T  A  *   356

1444  AATCGATCTCGAGTCTCGGCGATCGACCATCGGTCCCCATCTGGCACGGACGGTCATGCGAGGGTCGGCGTCCCGTCCGCCTCGGTCCT  1537
```

FIG. 3B

```
                                 177                                                              209
PheDH, Rh. M4                    L T V L V Q G L G A V G G S L A A E A G - - A Q - L L V A D T D T
PheDH, T. intermedius            R V V A I Q G V G K V G E R L L Q L L V E V G - - A Y - C K I A D I D S
PheDH, B. sphaericus             K T Y A I Q G L G K V G Y K V A E Q L L K A G - - A D - L F V Y D I H E
PheDH, S. ureae                  R K Y S I Q G L A K V G Y K V A E H I I N E G - - G K - L M L T D I N E
LeuDH, B. stearothermophilus     K V V A V Q G V G N V A Y H L C R H L H E E G - - A K - L I V T D I N K
GluDH, C. symbiosum              T - V A L A G F G N V A W G A A K K L A E L G A K A V T L S G P D G Y I
GluDH, C. difficile              K - I A V Q G I G N V G S Y T V L N C E K L G - - G T V V A M A E W C K
GluDH, E. coli                   R - V S V S G S G N V A Q Y A I E K A M E F G - - A R V I T A S D S S G
GluDH, N. crassa                 R - V A L S G S G N V A Q Y A A L K L I E L G - - A T V V S L S D S K G
GluDH, bovine and human          K T F A V Q G F G N V G L H S M R Y L G R F G A K C V A V G E S D G S I
AlaDH, B. sphaericus             K - V T V I G G I A G T N A A K I A V G M G - - A D - V T V I D L S P
AlaDH, B. stearothermophilus     K - V T I I G G T A G T N A A K I G V G L G - - A D - V T I L D I N A
                                     *   *   *   *   *   *   *   *   *        *       *         *
                                 |—βG—|  |————α10————|                              |—βH——|
```

FIG. 4

```
                          33                                                                            75
PheDH, Rh. M4             T Q L G P A A G G T R A A Q Y S Q L A D A L T D A G K - L A G A M T L K M A V S N L P M
PheDH, T. intermedius     T T A G P A L G G C R M I P Y A S T D E A L E D V L R - L S K G M T Y K C S L A D V D F
PheDH, B. sphaericus      T T L G P A L G G T R M Y P Y K N V D E A L E D V L R - L S E G M T Y K C A A A D I D F
PheDH, S. ureae           R L W D L H S V D V S M A P Y K T M D L A L K D V L R - L S K G M T Y K C A A A D V D F
LeuDH, B. stearothermophilus  T T L G P A L G G T R M W M Y N S E E A L E D A L R - L A R G M T Y K N A A A G L N L GluDH, C. symbiosum       V Q F N G A I G P Y K G G L R F A P S V N L S I M - K F L G F E Q A F K D S L T T L P M
GluDH, C. difficile       S Q H N D A V G P T K G G I R F H Q N V S R D E V - K A L S I W M T F K C S V T G I P Y
GluDH, E. coli            V Q F S S A I G P Y K G G M R F H P S V N L S I L - K F L G F E Q T F K N A L T T L P M
GluDH, N. crassa          V Q F N S A L G P Y K G G L R L H P S V N L S I L - K F L G F E Q I F K N A L T G L S M
GluDH, bovine and human   A Q H S H Q R T P C K G G I R Y S T D V S V D E V - K A L A S L M T Y K C A V V D V P F AlaDH, B. sphaericus      D K K V V G I A Y E T V Q L A N G S L P L L T P M S E V A G K M A T Q I G A Q Y L E K N
AlaDH, B. stearothermophilus  E Q K V V G I A Y E T V Q L A N G S L P L L T P M S E V A G R M S V Q V G A Q F L E K P
                          |—βb—|        |————βc————|                            |————α6————|
```

FIG. 5A

|  | 76 | | | | | | | | | | | | | | | | | | | | | | | | 126 |
|---|---|---|---|---|---|---|---|---|---|---|---|---|---|---|---|---|---|---|---|---|---|---|---|---|---|
| PheDH, Rh. M4 | G G G K S V I A L P A P R H S I D P S T W A R I L R I H A E N | T | D K L S G N | Y | W | T G P D V N T N S A D |
| PheDH, T. intermedius | G G G K M V I I | G | D P K K | D | K S P E - - - - L F R V I G R | F | V G G L N G R | F | Y | T G T D M G T N P E D |
| PheDH, B. sphaericus | G G G K A V I I | G | D P E K | D | K S P A - - - - L F R A F G Q | F | V E S L N G R | F | Y | T G T D M G T T M D D |
| PheDH, S. ureae | G G G K S V I I | G | D P L K | D | K T P E - - - - K F R A F G Q | F | H E S L N G R | F | Y | T G T D M G T T L E D |
| LeuDH, B. stearothermophilus | G G G K T V I I | G | D P R K | D | K N E A - - - - M F R A F G R | F | Q G L N G R | Y | I T A E D V G | T | V A D |
| GluDH, C. symbiosum | G G A K G | G | S D F D P N G K S D R | E | - - - - - V M R F C Q A F M T E L Y R H - - | I | G P D I | D | V | P | A G D |
| GluDH, C. difficile | G G G K G | G | I H I V D P S T L S Q G | E | - - - - - L E R L S R G Y I D G I Y K L - - | I | G E K V D | V | P | A P D |
| GluDH, E. coli | G G G K G | G | S D F D P - K G K S - | E | - - - - G E V M R F C Q A L M T E L Y R H - - | L | G A D T D | V | P | A G D |
| GluDH, N. crassa | G G G K G | G | A D F D P - K G K S D A E - - - - - I R R F C C A F M A E L H K H - - | I | G A D T D | V | P | A G D |
| GluDH, bovine and human | G G A K A | G | V K K I N P - K - N Y T | D | - - - - - E D L E K I T R R F T M E L A - - K K G F I G - | P | G V D |
| AlaDH, B. sphaericus | H G G K G I L L G G V S G V H A R K V T V I G G G I A G T N A A K I A V G M G A D V T V I D L S P E R |
| AlaDH, B. stearothermophilus | H G G K G I L L G G V P G V R R G K V T I I G G G T A G T N A A K I G V G L G A D V T I L D I N A E R |

FIG. 5B

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 1294
        ( B ) TYPE: NUCLEIC ACID
        ( C ) STRANDEDNESS: DOUBLE
        ( D ) TOPOLOGY: LINEAR ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: RHODOCOCCUS SP. M4
        ( B ) INDIVIDUAL ISOLATE: PHENYLALANINE DEHYDROGENASE ( x i ) SEQUENCE DESCRIPTION: SEQ ID NO: 1:

```
CT  GCA  GAG  ACG  TTT  TCG  CCA  AAG  ACT  GGT  CAC  ACT  ATG  AAG  ACG  CAC                        47

CCT  CCG  TCG  CCG  CGG  ACC  CGA  ATC  GGG  ACT  GCT  CGG  AGT  TGT  CTG  CGT                        95

CCA  CTG  CAT  CCA  TCG  AAC  ATC  AAG  GGG  TAC  ATC  ATG  AGT  ATC  GAC  AGC                       143
                                                            Met  Ser  Ile  Asp  Ser
                                                             1                    5

GCA  CTG  AAC  TGG  GAC  GGG  GAA  ATG  ACG  GTC  ACC  CGA  TTC  GAC  CGG  GAG                       191
Ala  Leu  Asn  Trp  Asp  Gly  Glu  Met  Thr  Val  Thr  Arg  Phe  Asp  Arg  Glu
                    10                       15                            20

ACT  GGT  GCC  CAT  TTC  GTC  ATT  CGA  CTC  GAT  TCG  ACC  CAA  CTC  GGA  CCG                       239
Thr  Gly  Ala  His  Phe  Val  Ile  Arg  Leu  Asp  Ser  Thr  Gln  Leu  Gly  Pro
               25                       30                       35
```

| | | | | | | | | | | | | | | | | |
|---|---|---|---|---|---|---|---|---|---|---|---|---|---|---|---|---|
| GCG | GCC | GGA | GGC | ACC | AGA | GCC | GCA | CAG | TAC | TCA | CAG | CTG | GCG | GAC | GCC | 287 |
| Ala | Ala | Gly | Gly | Thr | Arg | Ala | Ala | Gln | Tyr | Ser | Gln | Leu | Ala | Asp | Ala | |
| | | | 40 | | | | 45 | | | | | 50 | | | | |
| CTC | ACC | GAC | GCC | GGC | AAA | TTG | GCG | GGG | GCG | ATG | ACG | TTG | AAG | ATG | GCA | 335 |
| Leu | Thr | Asp | Ala | Gly | Lys | Leu | Ala | Gly | Ala | Met | Thr | Leu | Lys | Met | Ala | |
| | 55 | | | | 60 | | | | | 65 | | | | | | |
| GTG | AGC | AAC | CTT | CCG | ATG | GGC | GGG | GGC | AAA | TCC | GTC | ATT | GCG | CTT | CCT | 383 |
| Val | Ser | Asn | Leu | Pro | Met | Gly | Gly | Gly | Lys | Ser | Val | Ile | Ala | Leu | Pro | |
| 70 | | | | | 75 | | | | | 80 | | | | | 85 | |
| GCG | CCG | CGT | CAT | TCG | ATC | GAT | CCG | AGC | ACG | TGG | GCA | CGC | ATC | CTC | CGA | 431 |
| Ala | Pro | Arg | His | Ser | Ile | Asp | Pro | Ser | Thr | Trp | Ala | Arg | Ile | Leu | Arg | |
| | | | | 90 | | | | | 95 | | | | | 100 | | |
| ATC | CAC | GCC | GAG | AAC | ATC | GAC | AAG | TTG | TCC | GGC | AAC | TAC | TGG | ACC | GGA | 479 |
| Ile | His | Ala | Glu | Asn | Ile | Asp | Lys | Leu | Ser | Gly | Asn | Tyr | Trp | Thr | Gly | |
| | | | | 105 | | | | 110 | | | | | 115 | | | |
| CCG | GAC | GTC | AAC | ACC | AAT | TCG | GCA | GAC | ATG | GAT | ACT | CTG | AAC | GAC | ACC | 527 |
| Pro | Asp | Val | Asn | Thr | Asn | Ser | Ala | Asp | Met | Asp | Thr | Leu | Asn | Asp | Thr | |
| | | | 120 | | | | | 125 | | | | | 130 | | | |
| ACC | GAG | TTC | GTG | TTC | GGA | CGG | TCG | CTC | GAA | CGC | GGC | GGC | GCG | GGT | TCG | 575 |
| Thr | Glu | Phe | Val | Phe | Gly | Arg | Ser | Leu | Glu | Arg | Gly | Gly | Ala | Gly | Ser | |
| | | 135 | | | | | 140 | | | | | 145 | | | | |
| AGC | GCG | TTC | ACC | ACC | GCC | GTT | GGC | GTG | TTC | GAG | GCG | ATG | AAG | GCG | ACC | 623 |
| Ser | Ala | Phe | Thr | Thr | Ala | Val | Gly | Val | Phe | Glu | Ala | Met | Lys | Ala | Thr | |
| 150 | | | | | 155 | | | | | 160 | | | | | 165 | |
| GTC | GCG | CAC | CGT | GGG | CTG | GGC | TCA | CTC | GAC | GGT | TTG | ACG | GTC | CTG | GTC | 671 |
| Val | Ala | His | Arg | Gly | Leu | Gly | Ser | Leu | Asp | Gly | Leu | Thr | Val | Leu | Val | |
| | | | | 170 | | | | | 175 | | | | | 180 | | |
| CAA | GGA | CTG | GGG | GCA | GTC | GGA | GGA | TCA | TTG | GCA | TCC | CTG | GCC | GCC | GAA | 719 |
| Gln | Gly | Leu | Gly | Ala | Val | Gly | Gly | Ser | Leu | Ala | Ser | Leu | Ala | Ala | Glu | |
| | | | 185 | | | | | 190 | | | | | 195 | | | |
| GCG | GGT | GCG | CAA | CTC | CTG | GTG | GCA | GAC | ACC | GAC | ACC | GAG | CGA | GTA | GCG | 767 |
| Ala | Gly | Ala | Gln | Leu | Leu | Val | Ala | Asp | Thr | Asp | Thr | Glu | Arg | Val | Ala | |
| | | 200 | | | | | 205 | | | | | 210 | | | | |
| CAC | GCT | GTT | GCG | TTG | GGC | CAC | ACA | GCG | GTT | GCC | CTC | GAG | GAC | GTT | CTG | 815 |
| His | Ala | Val | Ala | Leu | Gly | His | Thr | Ala | Val | Ala | Leu | Glu | Asp | Val | Leu | |
| | | | 215 | | | | | 220 | | | | | 225 | | | |
| TCC | ACC | CCG | TGT | GAT | GTC | TTC | GCA | CCC | TGC | GCA | ATG | GGC | GGC | GTC | ATC | 863 |
| Ser | Thr | Pro | Cys | Asp | Val | Phe | Ala | Pro | Cys | Ala | Met | Gly | Gly | Val | Ile | |
| 230 | | | | | 235 | | | | | 240 | | | | | 245 | |
| ACC | ACC | GAG | GTG | GCG | CGA | ACA | CTC | GAC | TGT | TCC | GTC | GTG | GCC | GGT | GCC | 911 |
| Thr | Thr | Glu | Val | Ala | Arg | Thr | Leu | Asp | Cys | Ser | Val | Val | Ala | Gly | Ala | |
| | | | | 250 | | | | | 255 | | | | | 260 | | |
| GCC | AAC | AAC | GTC | ATC | GCC | GAC | GAG | GCC | GCC | TCG | GAC | ATC | CTG | CAC | GCA | 959 |
| Ala | Asn | Asn | Val | Ile | Ala | Asp | Glu | Ala | Ala | Ser | Asp | Ile | Leu | His | Ala | |
| | | | 265 | | | | | 270 | | | | | 275 | | | |
| CGC | GGA | ATT | CTG | TAC | GCT | CCC | GAC | TTC | GTG | GCC | AAC | GCC | GGC | GGT | GCC | 1007 |
| Arg | Gly | Ile | Leu | Tyr | Ala | Pro | Asp | Phe | Val | Ala | Asn | Ala | Gly | Gly | Ala | |
| | | 280 | | | | | 285 | | | | | 290 | | | | |
| ATC | CAC | CTC | GTA | GGC | CGG | GAG | GTT | CTC | GGT | TGG | TCC | GAG | TCG | GTT | GTC | 1055 |
| Ile | His | Leu | Val | Gly | Arg | Glu | Val | Leu | Gly | Trp | Ser | Glu | Ser | Val | Val | |
| | | 295 | | | | 300 | | | | | 305 | | | | | |
| CAC | GAA | CGA | GCA | GTT | GCC | ATA | GGC | GAC | ACC | CTG | AAT | CAG | GTC | TTC | GAG | 1103 |
| His | Glu | Arg | Ala | Val | Ala | Ile | Gly | Asp | Thr | Leu | Asn | Gln | Val | Phe | Glu | |
| 310 | | | | | 315 | | | | | 320 | | | | | 325 | |
| ATC | TCC | GAC | AAC | GAC | GGC | GTC | ACC | CCG | GAC | GAG | GCC | GCC | CGC | ACT | CTC | 1151 |
| Ile | Ser | Asp | Asn | Asp | Gly | Val | Thr | Pro | Asp | Glu | Ala | Ala | Arg | Thr | Leu | |
| | | | | 330 | | | | | 335 | | | | | 340 | | |
| GCT | GGA | CGG | CGC | GCC | CGC | GAG | GCC | TCG | ACA | ACG | ACA | GCG | ACT | GCC | TAG | 1199 |
| Ala | Gly | Arg | Arg | Ala | Arg | Glu | Ala | Ser | Thr | Thr | Thr | Ala | Thr | Ala | | |
| | | | 345 | | | | | 350 | | | | | 355 | | | |

```
        TAA TCG ATC TCG GAG TCT GGC GAT CGA CCA TCG GTC CCC ATC TGG CAC    1247

GGA CGG TCA TGC GAG GGT CGG CGT CCC GTC CAG TCC GCC TCG GTC CT     1294
```

( 2 ) INFORMATION FOR SEQ ID NO:2:

( i ) SEQUENCE CHARACTERISTICS:
        ( A ) LENGTH: 356
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: RHODOCOCCUS SP.M4
        ( B ) INDIVIDUAL ISOLATE: PHENYLALANINE DEHYDROGENASE ( x i ) SEQUENCE DESCRIPTION: SEQ ID NO: 2:

```
Met Ser Ile Asp Ser Ala Leu Asn Trp Asp Gly Glu Met Thr Val Thr
 1               5                  10                  15

Arg Phe Asp Arg Glu Thr Gly Ala His Phe Val Ile Arg Leu Asp Ser
            20                  25                  30

Thr Gln Leu Gly Pro Ala Ala Gly Gly Thr Arg Ala Ala Gln Tyr Ser
        35                  40                  45

Gln Leu Ala Asp Ala Leu Thr Asp Ala Gly Lys Leu Ala Gly Ala Met
    50                  55                  60

Thr Leu Lys Met Ala Val Ser Asn Leu Pro Met Gly Gly Gly Lys Ser
 65                  70                  75                  80

Val Ile Ala Leu Pro Ala Pro Arg His Ser Ile Asp Pro Ser Thr Trp
                85                  90                  95

Ala Arg Ile Leu Arg Ile His Ala Glu Asn Ile Asp Lys Leu Ser Gly
            100                 105                 110

Asn Tyr Trp Thr Gly Pro Asp Val Asn Thr Asn Ser Ala Asp Met Asp
        115                 120                 125

Thr Leu Asn Asp Thr Thr Glu Phe Val Phe Gly Arg Ser Leu Glu Arg
    130                 135                 140

Gly Gly Ala Gly Ser Ser Ala Phe Thr Thr Ala Val Gly Val Phe Glu
145                 150                 155                 160

Ala Met Lys Ala Thr Val Ala His Arg Gly Leu Gly Ser Leu Asp Gly
                165                 170                 175

Leu Thr Val Leu Val Gln Gly Leu Gly Ala Val Gly Gly Ser Leu Ala
            180                 185                 190

Ser Leu Ala Ala Glu Ala Gly Ala Gln Leu Leu Val Ala Asp Thr Asp
        195                 200                 205

Thr Glu Arg Val Ala His Ala Val Ala Leu Gly His Thr Ala Val Ala
    210                 215                 220

Leu Glu Asp Val Leu Ser Thr Pro Cys Asp Val Phe Ala Pro Cys Ala
225                 230                 235                 240

Met Gly Gly Val Ile Thr Thr Glu Val Ala Arg Thr Leu Asp Cys Ser
                245                 250                 255

Val Val Ala Gly Ala Ala Asn Asn Val Ile Ala Asp Glu Ala Ala Ser
            260                 265                 270

Asp Ile Leu His Ala Arg Gly Ile Leu Tyr Ala Pro Asp Phe Val Ala
        275                 280                 285

Asn Ala Gly Gly Ala Ile His Leu Val Gly Arg Glu Val Leu Gly Trp
    290                 295                 300
```

```
Ser  Glu  Ser  Val  Val  His  Glu  Arg  Ala  Val  Ala  Ile  Gly  Asp  Thr  Leu
305                      310                      315                      320

Asn  Gln  Val  Phe  Glu  Ile  Ser  Asp  Asn  Asp  Gly  Val  Thr  Pro  Asp  Glu
               325                      330                      335

Ala  Ala  Arg  Thr  Leu  Ala  Gly  Arg  Arg  Ala  Arg  Glu  Ala  Ser  Thr  Thr
               340                      345                      350

Thr  Ala  Thr  Ala
          355
```

( 2 ) INFORMATION FOR SEQ ID NO:3:

( i ) SEQUENCE CHARACTERISTICS:
        ( A ) LENGTH: 33
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: RHODOCOCCUS SP.M4
        ( B ) INDIVIDUAL ISOLATE: PHENYLALANINE DEHYDROGENASE ( x i ) SEQUENCE DESCRIPTION: SEQ ID NO: 3:

```
Leu  Thr  Val  Leu  Val  Gln  Gly  Leu  Gly  Ala  Val  Gly  Gly  Ser  Leu  Ala
 1                   5                        10                       15

Ser  Leu  Ala  Ala  Glu  Ala  Gly  Ala  Gln  Leu  Leu  Val  Ala  Asp  Thr  Asp
               20                        25                       30

Thr
```

( 2 ) INFORMATION FOR SEQ ID NO:4:

( i ) SEQUENCE CHARACTERISTICS:
        ( A ) LENGTH: 33
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: T. INTERMEDIUS
        ( B ) INDIVIDUAL ISOLATE: PHENYLALANINE DEHYDROGENASE ( x i ) SEQUENCE DESCRIPTION: SEQ ID NO: 4:

```
Arg  Val  Val  Ala  Ile  Gln  Gly  Val  Gly  Lys  Val  Gly  Glu  Arg  Leu  Leu
 1                   5                        10                       15

Gln  Leu  Leu  Val  Glu  Val  Gly  Ala  Tyr  Cys  Lys  Ile  Ala  Asp  Ile  Asp
               20                        25                       30

Ser
```

( 2 ) INFORMATION FOR SEQ ID NO:5:

( i ) SEQUENCE CHARACTERISTICS:
        ( A ) LENGTH: 33
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: B. SPHAERICUS (B) INDIVIDUAL ISOLATE: PHENYLALANINE DEHYDROGENASE (xi) SEQUENCE DESCRIPTION: SEQ ID NO: 5:

```
Lys Thr Tyr Ala Ile Gln Gly Leu Gly Lys Val Gly Tyr Lys Val Ala
 1               5                  10                  15
Glu Gln Leu Leu Lys Ala Gly Ala Asp Leu Phe Val Tyr Asp Ile His
            20                  25                  30
Glu
```

(2) INFORMATION FOR SEQ ID NO:6:

(i) SEQUENCE CHARACTERISTICS:
        (A) LENGTH: 33
        (B) TYPE: AMINO ACID
        (D) TOPOLOGY: LINEAR (ii) MOLECULE TYPE:
        (A) DESCRIPTION: PROTEIN (iii) HYPOTHETICAL: NO (vi) ORIGINAL SOURCE:
        (A) ORGANISM: S. UREAE
        (B) INDIVIDUAL ISOLATE: PHENYLALANINE DEHYDROGENASE (xi) SEQUENCE DESCRIPTION: SEQ ID NO: 6:

```
Arg Lys Tyr Ser Ile Gln Gly Leu Ala Lys Val Gly Tyr Lys Val Ala
 1               5                  10                  15
Glu His Ile Ile Asn Glu Gly Gly Lys Leu Met Leu Thr Asp Ile Asn
            20                  25                  30
Glu
```

(2) INFORMATION FOR SEQ ID NO:7:

(i) SEQUENCE CHARACTERISTICS:
        (A) LENGTH: 33
        (B) TYPE: AMINO ACID
        (D) TOPOLOGY: LINEAR (ii) MOLECULE TYPE:
        (A) DESCRIPTION: PROTEIN (iii) HYPOTHETICAL: NO (vi) ORIGINAL SOURCE:
        (A) ORGANISM: S. STEAROTHERMOPHILUS
        (B) INDIVIDUAL ISOLATE: LEUCINE DEHYDROGENASE (xi) SEQUENCE DESCRIPTION: SEQ ID NO: 7:

```
Lys Val Val Ala Val Gln Gly Val Gly Asn Val Ala Tyr His Leu Cys
 1               5                  10                  15
Arg His Leu His Glu Glu Gly Ala Lys Leu Ile Val Thr Asp Ile Asn
            20                  25                  30
Lys
```

(2) INFORMATION FOR SEQ ID NO:8:

(i) SEQUENCE CHARACTERISTICS:
        (A) LENGTH: 35
        (B) TYPE: AMINO ACID
        (D) TOPOLOGY: LINEAR (ii) MOLECULE TYPE:
        (A) DESCRIPTION: PROTEIN (iii) HYPOTHETICAL: NO (vi) ORIGINAL SOURCE:

(A) ORGANISM: C. SYMBIOSUM
(B) INDIVIDUAL ISOLATE: GLUTAMATE DEHYDROGENASE (xi) SEQUENCE DESCRIPTION: SEQ ID NO: 8:

Thr Val Ala Leu Ala Gly Phe Gly Asn Val Ala Trp Gly Ala Ala Lys
 1               5                  10                  15
Lys Leu Ala Glu Leu Gly Ala Lys Ala Val Thr Leu Ser Gly Pro Asp
             20                  25                  30
Gly Tyr Ile
         35

(2) INFORMATION FOR SEQ ID NO:9:

(i) SEQUENCE CHARACTERISTICS:
      (A) LENGTH: 33
      (B) TYPE: AMINO ACID
      (D) TOPOLOGY: LINEAR (ii) MOLECULE TYPE:
      (A) DESCRIPTION: PROTEIN (iii) HYPOTHETICAL: NO (vi) ORIGINAL SOURCE:
      (A) ORGANISM: C. DIFFICILE
      (B) INDIVIDUAL ISOLATE: GLUTAMATE DEHYDROGENASE (xi) SEQUENCE DESCRIPTION: SEQ ID NO: 9:

Lys Ile Ala Val Gln Gly Ile Gly Asn Val Gly Ser Tyr Thr Val Leu
 1               5                  10                  15
Asn Cys Glu Lys Leu Gly Gly Thr Val Val Ala Met Ala Glu Trp Cys
             20                  25                  30
Lys (2) INFORMATION FOR SEQ ID NO:10:

(i) SEQUENCE CHARACTERISTICS:
      (A) LENGTH: 33
      (B) TYPE: AMINO ACID
      (D) TOPOLOGY: LINEAR (ii) MOLECULE TYPE:
      (A) DESCRIPTION: PROTEIN (iii) HYPOTHETICAL: NO (vi) ORIGINAL SOURCE:
      (A) ORGANISM: E. COLI
      (B) INDIVIDUAL ISOLATE: GLUTAMATE DEHYDROGENASE (xi) SEQUENCE DESCRIPTION: SEQ ID NO: 10:

Arg Val Ser Val Ser Gly Ser Gly Asn Val Ala Gln Tyr Ala Ile Glu
 1               5                  10                  15
Lys Ala Met Glu Phe Gly Ala Arg Val Ile Thr Ala Ser Asp Ser Ser
             20                  25                  30
Gly (2) INFORMATION FOR SEQ ID NO:11:

(i) SEQUENCE CHARACTERISTICS:
      (A) LENGTH: 33
      (B) TYPE: AMINO ACID
      (D) TOPOLOGY: LINEAR (ii) MOLECULE TYPE:
      (A) DESCRIPTION: PROTEIN (iii) HYPOTHETICAL: NO ( v i ) ORIGINAL SOURCE:
    ( A ) ORGANISM: N. CRASSA
    ( B ) INDIVIDUAL ISOLATE: GLUTAMATE DEHYDROGENASE ( x i ) SEQUENCE DESCRIPTION: SEQ ID NO: 11:

```
Arg Val Ala Leu Ser Gly Ser Gly Asn Val Ala Gln Tyr Ala Ala Leu
 1               5                   10                  15

Lys Leu Ile Glu Leu Gly Ala Thr Val Val Ser Leu Ser Asp Ser Lys
            20                  25                  30

Gly
```

( 2 ) INFORMATION FOR SEQ ID NO:12:

( i ) SEQUENCE CHARACTERISTICS:
        ( A ) LENGTH: 36
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: BOVINE AND HUMAN
        ( B ) INDIVIDUAL ISOLATE: GLUTAMATE DEHYDROGENASE ( x i ) SEQUENCE DESCRIPTION: SEQ ID NO: 12:

```
Lys Thr Phe Ala Val Gln Gly Phe Gly Asn Val Gly Leu His Ser Met
 1               5                   10                  15

Arg Tyr Leu Gly Arg Phe Gly Ala Lys Cys Val Ala Val Gly Glu Ser
            20                  25                  30

Asp Gly Ser Ile
            35
```

( 2 ) INFORMATION FOR SEQ ID NO:13:

( i ) SEQUENCE CHARACTERISTICS:
        ( A ) LENGTH: 32
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: B. SPHAERICUS
        ( B ) INDIVIDUAL ISOLATE: ALANINE DEHYDROGENASE ( x i ) SEQUENCE DESCRIPTION: SEQ ID NO: 13:

```
Lys Val Thr Val Ile Gly Gly Gly Ile Ala Gly Thr Asn Ala Ala Lys
 1               5                   10                  15

Ile Ala Val Gly Met Gly Ala Asp Val Thr Val Ile Asp Leu Ser Pro
            20                  25                  30
```

( 2 ) INFORMATION FOR SEQ ID NO:14:

( i ) SEQUENCE CHARACTERISTICS:
        ( A ) LENGTH: 32
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
    ( A ) ORGANISM: B. STEAROTHERMOPHILUS
    ( B ) INDIVIDUAL ISOLATE: ALANINE DEHYDROGENASE ( x i ) SEQUENCE DESCRIPTION: SEQ ID NO: 14:

```
Lys Val Thr Ile Ile Gly Gly Gly Thr Ala Gly Thr Asn Ala Ala Lys
 1               5                  10                  15
Ile Gly Val Gly Leu Gly Ala Asp Val Thr Ile Leu Asp Ile Asn Ala
            20                  25                  30
```

( 2 ) INFORMATION FOR SEQ ID NO:15:

( i ) SEQUENCE CHARACTERISTICS:
        ( A ) LENGTH: 94
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: RHODOCOCCUS SP.M4
        ( B ) INDIVIDUAL ISOLATE: PHENYLALANINE DEHYDROGENASE ( x i ) SEQUENCE DESCRIPTION: SEQ ID NO: 15:

```
Thr Gln Leu Gly Pro Ala Ala Gly Gly Thr Arg Ala Ala Gln Tyr Ser
 1               5                  10                  15
Gln Leu Ala Asp Ala Leu Thr Asp Ala Gly Lys Leu Ala Gly Ala Met
            20                  25                  30
Thr Leu Lys Met Ala Val Ser Asn Leu Pro Met Gly Gly Gly Lys Ser
            35                  40                  45
Val Ile Ala Leu Pro Ala Pro Arg His Ser Ile Asp Pro Ser Thr Trp
            50                  55                  60
Ala Arg Ile Leu Arg Ile His Ala Glu Asn Ile Asp Lys Leu Ser Gly
 65                 70                  75                  80
Asn Tyr Trp Thr Gly Pro Asp Val Asn Thr Asn Ser Ala Asp
            85                  90
```

( 2 ) INFORMATION FOR SEQ ID NO:16:

( i ) SEQUENCE CHARACTERISTICS:
        ( A ) LENGTH: 89
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: T. INTERMEDIUS
        ( B ) INDIVIDUAL ISOLATE: PHENYLALANINE DEHYDROGENASE ( x i ) SEQUENCE DESCRIPTION: SEQ ID NO: 16:

```
Thr Thr Ala Gly Pro Ala Leu Gly Gly Cys Arg Met Ile Pro Tyr Ala
 1               5                  10                  15
Ser Thr Asp Glu Ala Leu Glu Asp Val Leu Arg Leu Ser Lys Gly Met
            20                  25                  30
Thr Tyr Lys Cys Ser Leu Ala Asp Val Asp Phe Gly Gly Gly Lys Met
            35                  40                  45
Val Ile Ile Gly Asp Pro Lys Lys Asp Lys Ser Pro Glu Leu Phe Arg
            50                  55                  60
```

```
            Val   Ile   Gly   Arg   Phe   Val   Gly   Gly   Leu   Asn   Gly   Arg   Phe   Tyr   Thr   Gly
             65                      70                            75                                  80

Thr   Asp   Met   Gly   Thr   Asn   Pro   Glu   Asp
                                          85
```

(2) INFORMATION FOR SEQ ID NO:17:

(i) SEQUENCE CHARACTERISTICS:
        (A) LENGTH: 89
        (B) TYPE: AMINO ACID
        (D) TOPOLOGY: LINEAR (ii) MOLECULE TYPE:
        (A) DESCRIPTION: PROTEIN (iii) HYPOTHETICAL: NO (vi) ORIGINAL SOURCE:
        (A) ORGANISM: B. SPHAERICUS
        (B) INDIVIDUAL ISOLATE: PHENYLALANINE DEHYDROGENASE (xi) SEQUENCE DESCRIPTION: SEQ ID NO: 17:

```
            Thr   Thr   Leu   Gly   Pro   Ala   Leu   Gly   Gly   Thr   Arg   Met   Tyr   Pro   Tyr   Lys
             1                       5                            10                                  15

Asn   Val   Asp   Glu   Ala   Leu   Glu   Asp   Val   Leu   Arg   Leu   Ser   Glu   Gly   Met
                                    20                            25                      30

Thr   Tyr   Lys   Cys   Ala   Ala   Ala   Asp   Ile   Asp   Phe   Gly   Gly   Gly   Lys   Ala
                         35                            40                            45

Val   Ile   Ile   Gly   Asp   Pro   Glu   Lys   Asp   Lys   Ser   Pro   Ala   Leu   Phe   Arg
                   50                            55                            60

Ala   Phe   Gly   Gln   Phe   Val   Glu   Ser   Leu   Asn   Gly   Arg   Phe   Tyr   Thr   Gly
             65                      70                            75                                  80

Thr   Asp   Met   Gly   Thr   Thr   Met   Asp   Asp
                                          85
```

(2) INFORMATION FOR SEQ ID NO:18:

(i) SEQUENCE CHARACTERISTICS:
        (A) LENGTH: 89
        (B) TYPE: AMINO ACID
        (D) TOPOLOGY: LINEAR (ii) MOLECULE TYPE:
        (A) DESCRIPTION: PROTEIN (iii) HYPOTHETICAL: NO (vi) ORIGINAL SOURCE:
        (A) ORGANISM: S. UREAE
        (B) INDIVIDUAL ISOLATE: PHENYLALANINE DEHYDROGENASE (xi) SEQUENCE DESCRIPTION: SEQ ID NO: 18:

```
            Arg   Leu   Trp   Asp   Leu   His   Ser   Val   Asp   Val   Ser   Met   Ala   Pro   Tyr   Lys
             1                       5                            10                                  15

Thr   Met   Asp   Leu   Ala   Leu   Lys   Asp   Val   Leu   Arg   Leu   Ser   Lys   Gly   Met
                                    20                            25                      30

Thr   Tyr   Lys   Cys   Ala   Ala   Ala   Asp   Val   Asp   Phe   Gly   Gly   Gly   Lys   Ser
                         35                            40                            45

Val   Ile   Ile   Gly   Asp   Pro   Leu   Lys   Asp   Lys   Thr   Pro   Glu   Lys   Phe   Arg
                   50                            55                            60

Ala   Phe   Gly   Gln   Phe   Ile   Glu   Ser   Leu   Asn   Gly   Arg   Phe   Tyr   Thr   Gly
             65                      70                            75                                  80

Thr   Asp   Met   Gly   Thr   Thr   Leu   Glu   Asp
                                          85
```

( 2 ) INFORMATION FOR SEQ ID NO:19:

( i ) SEQUENCE CHARACTERISTICS:
        ( A ) LENGTH: 89
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: S. STEAROTHERMOPHILUS
        ( B ) INDIVIDUAL ISOLATE: LEUCINE DEHYDROGENASE ( x i ) SEQUENCE DESCRIPTION: SEQ ID NO: 19:

```
Thr Thr Leu Gly Pro Ala Leu Gly Gly Thr Arg Met Trp Met Tyr Asn
 1               5                   10                  15

Ser Glu Glu Glu Ala Leu Glu Asp Ala Leu Arg Leu Ala Arg Gly Met
            20                  25                  30

Thr Tyr Lys Asn Ala Ala Ala Gly Leu Asn Leu Gly Gly Gly Lys Thr
        35                  40                  45

Val Ile Ile Gly Asp Pro Arg Lys Asp Lys Asn Glu Ala Met Phe Arg
    50                  55                  60

Ala Phe Gly Arg Phe Ile Gln Gly Leu Asn Gly Arg Tyr Ile Thr Ala
65              70                  75                      80

Glu Asp Val Gly Thr Thr Val Ala Asp
                85
```

( 2 ) INFORMATION FOR SEQ ID NO:20:

( i ) SEQUENCE CHARACTERISTICS:
        ( A ) LENGTH: 87
        ( B ) TYPE: AMINO ACID
        ( D ) TOPOLOGY: LINEAR ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: C. SYMBIOSUM
        ( B ) INDIVIDUAL ISOLATE: GLUTAMATE DEHYDROGENASE ( x i ) SEQUENCE DESCRIPTION: SEQ ID NO: 20:

```
Val Gln Phe Asn Gly Ala Ile Gly Pro Tyr Lys Gly Gly Leu Arg Phe
 1               5                   10                  15

Ala Pro Ser Val Asn Leu Ser Ile Met Lys Phe Leu Gly Phe Glu Gln
            20                  25                  30

Ala Phe Lys Asp Ser Leu Thr Thr Leu Pro Met Gly Gly Ala Lys Gly
        35                  40                  45

Gly Ser Asp Phe Asp Pro Asn Gly Lys Ser Asp Arg Glu Val Met Arg
    50                  55                  60

Phe Cys Gln Ala Phe Met Thr Glu Leu Tyr Arg His Ile Gly Pro Asp
65              70                  75                      80

Ile Asp Val Pro Ala Gly Asp
                85
```

( 2 ) INFORMATION FOR SEQ ID NO:21:

( i ) SEQUENCE CHARACTERISTICS:
        ( A ) LENGTH: 87

(B) TYPE: AMINO ACID
(D) TOPOLOGY: LINEAR (ii) MOLECULE TYPE:
(A) DESCRIPTION: PROTEIN (iii) HYPOTHETICAL: NO (vi) ORIGINAL SOURCE:
(A) ORGANISM: C. DIFFICILE
(B) INDIVIDUAL ISOLATE: GLUTAMATE DEHYDROGENASE (xi) SEQUENCE DESCRIPTION: SEQ ID NO: 21:

```
Ser Gln His Asn Asp Ala Val Gly Pro Thr Lys Gly Gly Ile Arg Phe
 1               5                  10                    15
His Gln Asn Val Ser Arg Asp Glu Val Lys Ala Leu Ser Ile Trp Met
              20                  25                  30
Thr Phe Lys Cys Ser Val Thr Gly Ile Pro Tyr Gly Gly Gly Lys Gly
          35                  40                  45
Gly Ile Ile Val Asp Pro Ser Thr Leu Ser Gln Gly Glu Leu Glu Arg
      50                  55                  60
Leu Ser Arg Gly Tyr Ile Asp Gly Ile Tyr Lys Leu Ile Gly Glu Lys
 65                  70                  75                  80
Val Asp Val Pro Ala Pro Asp
              85
```

(2) INFORMATION FOR SEQ ID NO:22:

(i) SEQUENCE CHARACTERISTICS:
(A) LENGTH: 87
(B) TYPE: AMINO ACID
(D) TOPOLOGY: LINEAR (ii) MOLECULE TYPE:
(A) DESCRIPTION: PROTEIN (iii) HYPOTHETICAL: NO (vi) ORIGINAL SOURCE:
(A) ORGANISM: E. COLI
(B) INDIVIDUAL ISOLATE: GLUTAMATE DEHYDROGENASE (xi) SEQUENCE DESCRIPTION: SEQ ID NO: 22:

```
Val Gln Phe Ser Ser Ala Ile Gly Pro Tyr Lys Gly Gly Met Arg Phe
 1               5                  10                    15
His Pro Ser Val Asn Leu Ser Ile Leu Lys Phe Leu Gly Phe Glu Gln
              20                  25                  30
Thr Phe Lys Asn Ala Leu Thr Thr Leu Pro Met Gly Gly Gly Lys Gly
          35                  40                  45
Gly Ser Asp Phe Asp Pro Lys Gly Lys Ser Glu Gly Glu Val Met Arg
      50                  55                  60
Phe Cys Gln Ala Leu Met Thr Glu Leu Tyr Arg His Leu Gly Ala Asp
 65                  70                  75                  80
Thr Asp Val Pro Ala Gly Asp
              85
```

(2) INFORMATION FOR SEQ ID NO:23:

(i) SEQUENCE CHARACTERISTICS:
(A) LENGTH: 87
(B) TYPE: AMINO ACID
(D) TOPOLOGY: LINEAR (ii) MOLECULE TYPE:
(A) DESCRIPTION: PROTEIN (iii) HYPOTHETICAL: NO (vi) ORIGINAL SOURCE:
    (A) ORGANISM: N. CRASSA
    (B) INDIVIDUAL ISOLATE: GLUTAMATE DEHYDROGENASE (xi) SEQUENCE DESCRIPTION: SEQ ID NO: 23:

```
Val Gln Phe Asn Ser Ala Leu Gly Pro Tyr Lys Gly Gly Leu Arg Leu
 1               5                  10                  15

His Pro Ser Val Asn Leu Ser Ile Leu Lys Phe Leu Gly Phe Glu Gln
            20                  25                  30

Ile Phe Lys Asn Ala Leu Thr Gly Leu Ser Met Gly Gly Lys Gly
        35                  40                  45

Gly Ala Asp Phe Asp Pro Lys Gly Lys Ser Asp Ala Glu Ile Arg Arg
    50                  55                  60

Phe Cys Cys Ala Phe Met Ala Glu Leu His Lys His Ile Gly Ala Asp
65                  70                  75                  80

Thr Asp Val Pro Ala Gly Asp
                85
```

(2) INFORMATION FOR SEQ ID NO:24:

(i) SEQUENCE CHARACTERISTICS:
    (A) LENGTH: 84
    (B) TYPE: AMINO ACID
    (D) TOPOLOGY: LINEAR (ii) MOLECULE TYPE:
    (A) DESCRIPTION: PROTEIN (iii) HYPOTHETICAL: NO (vi) ORIGINAL SOURCE:
    (A) ORGANISM: BOVINE AND HUMAN
    (B) INDIVIDUAL ISOLATE: GLUTAMATE DEHYDROGENASE (xi) SEQUENCE DESCRIPTION: SEQ ID NO: 24:

```
Ala Gln His Ser His Gln Arg Thr Pro Cys Lys Gly Gly Ile Arg Tyr
 1               5                  10                  15

Ser Thr Asp Val Ser Val Asp Glu Val Lys Ala Leu Ala Ser Leu Met
            20                  25                  30

Thr Tyr Lys Cys Ala Val Val Asp Val Pro Phe Gly Gly Ala Lys Ala
        35                  40                  45

Gly Val Lys Ile Asn Pro Lys Asn Tyr Thr Asp Glu Asp Leu Glu Lys
    50                  55                  60

Ile Thr Arg Arg Phe Thr Met Glu Leu Ala Lys Lys Gly Phe Ile Gly
65                  70                  75                  80

Pro Gly Val Asp
```

(2) INFORMATION FOR SEQ ID NO:25:

(i) SEQUENCE CHARACTERISTICS:
    (A) LENGTH: 95
    (B) TYPE: AMINO ACID
    (D) TOPOLOGY: LINEAR (ii) MOLECULE TYPE:
    (A) DESCRIPTION: PROTEIN (iii) HYPOTHETICAL: NO (vi) ORIGINAL SOURCE:
    (A) ORGANISM: B. SPHAERICUS
    (B) INDIVIDUAL ISOLATE: ALANINE DEHYDROGENASE (xi) SEQUENCE DESCRIPTION: SEQ ID NO: 25:

```
Asp Lys Lys Val Val Gly Ile Ala Tyr Glu Thr Val Gln Leu Ala Asn
 1               5                   10                  15

Gly Ser Leu Pro Leu Leu Thr Pro Met Ser Glu Val Ala Gly Lys Met
             20              25                  30

Ala Thr Gln Ile Gly Ala Gln Tyr Leu Glu Lys Asn His Gly Gly Lys
         35              40                  45

Gly Ile Leu Leu Gly Gly Val Ser Gly Val His Ala Arg Lys Val Thr
     50              55                  60

Val Ile Gly Gly Gly Ile Ala Gly Thr Asn Ala Ala Lys Ile Ala Val
 65                  70              75                      80

Gly Met Gly Ala Asp Val Thr Val Ile Asp Leu Ser Pro Glu Arg
                 85                  90              95
```

(2) INFORMATION FOR SEQ ID NO:26:

(i) SEQUENCE CHARACTERISTICS:
        (A) LENGTH: 95
        (B) TYPE: AMINO ACID
        (D) TOPOLOGY: LINEAR (ii) MOLECULE TYPE:
        (A) DESCRIPTION: PROTEIN (iii) HYPOTHETICAL: NO (vi) ORIGINAL SOURCE:
        (A) ORGANISM: B. STEAROTHERMOPHILUS
        (B) INDIVIDUAL ISOLATE: ALANINE DEHYDROGENASE (xi) SEQUENCE DESCRIPTION: SEQ ID NO: 26:

```
Glu Gln Lys Val Val Gly Ile Ala Tyr Glu Thr Val Gln Leu Ala Asn
 1               5                   10                  15

Gly Ser Leu Pro Leu Leu Thr Pro Met Ser Glu Val Ala Gly Arg Met
             20              25                  30

Ser Val Gln Val Gly Ala Gln Phe Leu Glu Lys Pro His Gly Gly Lys
         35              40                  45

Gly Ile Leu Leu Gly Gly Val Pro Gly Val Arg Arg Gly Lys Val Thr
     50              55                  60

Ile Ile Gly Gly Gly Thr Ala Gly Thr Asn Ala Ala Lys Ile Gly Val
 65                  70              75                      80

Gly Leu Gly Ala Asp Val Thr Ile Leu Asp Ile Asn Ala Glu Arg
                 85                  90              95
```

(2) INFORMATION FOR SEQ ID NO:27:

(i) SEQUENCE CHARACTERISTICS:
        (A) LENGTH: 12
        (B) TYPE: AMINO ACID
        (D) TOPOLOGY: LINEAR (ii) MOLECULE TYPE:
        (A) DESCRIPTION: PEPTIDE (iii) HYPOTHETICAL: NO (vi) ORIGINAL SOURCE:
        (A) ORGANISM: RHODOCOCCUS SP. M4
        (B) INDIVIDUAL ISOLATE: PHENYLALANINE DEHYDROGENASE (xi) SEQUENCE DESCRIPTION: SEQ ID NO: 27:

```
Ser Ile Asp Ser Ala Leu Asn Trp Asp Gly Glu Met
 1               5                   10
```

(2) INFORMATION FOR SEQ ID NO:28:

```
( i ) SEQUENCE CHARACTERISTICS:
        ( A ) LENGTH: 11
        ( B ) TYPE: AMINO ACID
        ( D ) TOPOLOGY: LINEAR ( i i ) MOLECULE TYPE:
        ( A ) DESCRIPTION: PEPTIDE ( i i i ) HYPOTHETICAL: NO ( v i ) ORIGINAL SOURCE:
        ( A ) ORGANISM: RHODOCOCCUS SP. M4
        ( B ) INDIVIDUAL ISOLATE: PHENYLALANINE DEHYDROGENASE ( x i ) SEQUENCE DESCRIPTION: SEQ ID NO: 28:

Ala  Glu  Asn  Ile  Asp  Lys  Leu  Ser  Gly  Asn  Tyr
     1              5                             10
```

( 2 ) INFORMATION FOR SEQ ID NO:29:

```
( i ) SEQUENCE CHARACTERISTICS:
        ( A ) LENGTH: 18
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: RHODOCOCCUS SP. M4
        ( B ) INDIVIDUAL ISOLATE: PHENYLALANINE DEHYDROGENASE ( x i ) SEQUENCE DESCRIPTION: SEQ ID NO: 29:

ACCTGGGACG GGGAGATG                                                    18
```

( 2 ) INFORMATION FOR SEQ ID NO:30:

```
( i ) SEQUENCE CHARACTERISTICS:
        ( A ) LENGTH: 18
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: RHODOCOCCUS SP. M4
        ( B ) INDIVIDUAL ISOLATE: PHENYLALANINE DEHYDROGENASE ( x i ) SEQUENCE DESCRIPTION: SEQ ID NO: 30:

CTTGTCGATG TTCTCGGC                                                    18
```

NUCLEIC ACID ENCODING RHODOCOCCUS PHENYLALANINE DEHYDROGENASE

This invention was made under NIH Grant No. GM 33449. As such the Government has certain rights in the invention.

BACKGROUND OF INVENTION

L-Phenylalanine dehydrogenase is a member of a large family of amino acid dehydrogenase enzymes. It is an important enzyme for both medical and industrial applications. Purified bacterial L-phenylalanine dehydrogenase is currently used in enzyme-based assays for screening for hyperphenylalanemias such as phenylketonuria, in newborn infants. Phenylketonuria is a congenital defect in phenylalanine synthesis which is treated by implementation of a low phenylalanine diet. The efficacy of such diet programs is also monitored using an L-phenylalanine dehydrogenase-based enzymatic test. In addition, the enzyme is critical to the industrial synthesis of L-amino acids, e.g. L-phenylalanine, which is essential in the production of aspartame. The value of the worldwide aspartame market is estimated to be $1.2 billion.

L-Phenylalanine dehydrogenase is present in various forms in Gram-positive, aerobic bacteria. For example, in *Bacillus sphaericus* and *Sporosarcina ureae*, the enzyme exists as an octomer and in *Thermoactinomyces intermedius*, it exists as a hexamer. In *Rhodococcus*, L-phenylalanine dehydrogenase is known to exist as a tetramer composed of monomers of molecular weight 39.5 kDa (Brunhuber and Blanchard, *FASEB J.* 7: 1069 (1993)). To date, only the nucleotide sequences of L-phenylalanine dehydrogenases isolated from *Bacillus sphaericus* (Okazaki, et. al., *Gene* 63: 337–341 (1988)), *Sporosarcina ureae* (Hibino, et.al., U.S. Pat. No. 4,970,157 (1990)), and *Thermoactinomyces intermedius* (Takada, et.al., *J.Biochem.* 109: 371–376 (1991)) have been determined.

The present invention is based upon the elucidation of the nucleic acid sequence encoding L-phenylalanine dehydrogenase from *Rhodococcus*.

SUMMARY OF THE INVENTION

The present invention provides a purified and isolated nucleic acid encoding *Rhodococcus* L-phenylalanine dehydrogenase. The present invention also provides a vector comprising nucleic acid encoding *Rhodococcus* L-phenylalanine dehydrogenase. The present invention further provides a host cell transformed by a vector comprising nucleic acid encoding *Rhodococcus* L-phenylalanine dehydrogenase. Lastly, the present invention provides a method for producing recombinant *Rhodococcus* L-phenylalanine dehydrogenase comprising growing a host cell transformed with a vector comprising nucleic acid encoding *Rhodococcus* L-phenylalanine dehydrogenase in culture, and recovering L-phenylalanine dehydrogenase from the culture.

BRIEF DESCRIPTION OF THE FIGURES

FIG. 3 depicts the DNA sequence of the pdh gene from *Rhodococcus* sp. M4 (SEQ ID NO: 1) and deduced amino acid sequence (SEQ ID NO: 2). Protein sequences that were determined by automated Edman degradation are double-underlined. The consensus sequences of important restriction sites are underlined. A probable ribosome-binding site (RBS), 7 bp upstream from the initiation ATG codon, is also underlined.

FIG. 4 depicts a sequence comparison of pyridine nucleotide-binding regions of several NAD(P)$^+$-dependent amino acid dehydrogenases. Numbering is for the *Rhodococcus* enzyme. Secondary structure descriptions are based on the three-dimensional structure of *C.symbiosum* glutamate dehydrogenase (GluDH) (11). Conserved residues are indicated in boldface. Residues important to the formation of the Rossman fold are indicated by asterisks. Specific references are listed in Table II, with the addition of the following: phenylalanine dehydrogenase (PheDH) from *S.aureae* and glutamate dehydrogenase (GluDH) from *E.coli*, *Neurospora crassa*, and bovine/human. LeuDH, leucine dehydrogenase; AlaDH, alanine dehydrogenase.

FIG. 5 depicts a sequence comparison of conserved residues in putative catalytic domains of several amino acid dehydrogenases. Numbering is for the *Rhodococcus* enzyme. Secondary structure descriptions are based on three-dimensional structure of *C.symbiosum* glutamate dehydrogenase (GluDH). Conserved residues in all dehydrogenases are shown in boldface. Residues conserved in either the glutamate or phenylalanine (PheDH)/leucine (LeuDH) dehydrogenase are boxed. Specific references are as listed in the legend to FIG. 4. AlaDH, alanine dehydrogenase.

DETAILED DESCRIPTION OF THE INVENTION

Figure 1:
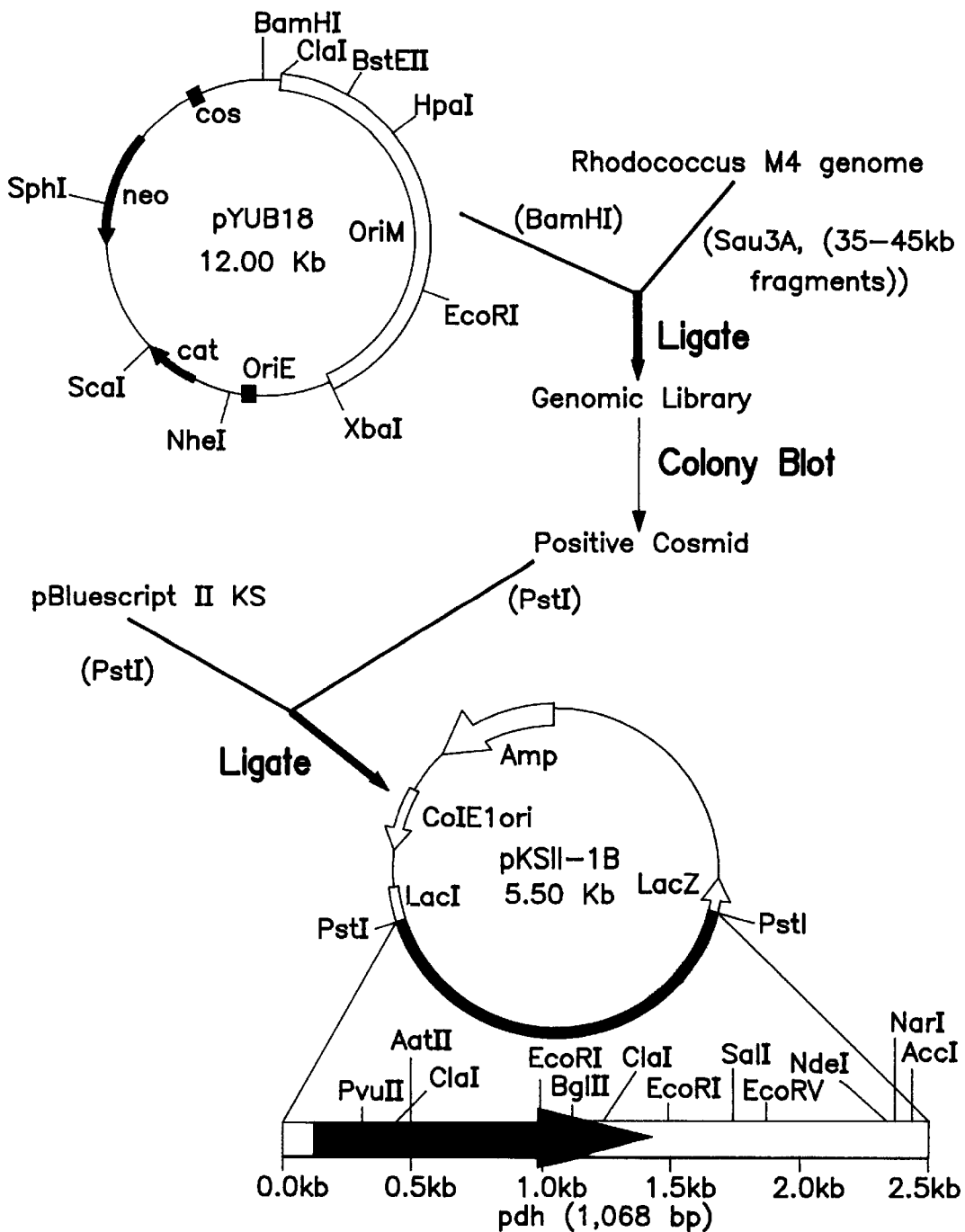
FIG. 1 depicts a schematic of *Rhodococcus* sp. M4 library generation and subsequent subcloning of the L-phenylalanine dehydrogenase (pdh) gene.

The present invention provides a purified and isolated nucleic acid encoding *Rhodococcus* L-phenylalanine dehydrogenase. The nucleic acid of the present invention can be genomic DNA, cDNA or RNA. In the preferred embodiment of the present invention, the nucleic acid encodes the amino acid sequence contained in FIG. 3, and in the most preferred embodiment, the nucleotide sequence contained in FIG. 3. As used herein, "encoding" means the ability of a nucleic acid to specify a particular amino acid sequence by virtue of the arrangement of nucleotides along its length. Accordingly, due to the degeneracy of the genetic code, the nucleic acid of the present invention includes a multitude of nucleic acids which will encode L-phenylalanine dehydrogenase. The specific substitutions in the nucleic acid sequence would be apparent to one skilled in the art.

The purified and isolated nucleic acid of the present invention encoding *Rhodococcus* phenylalanine dehydrogenase can be inserted into a vector and the vector introduced into a host cell. The term "inserted" as used herein means the ligation of a foreign DNA fragment and vector DNA by techniques such as the annealing of compatible cohesive ends generated by restriction endonuclease digestion or by use of blunt end ligation techniques. Other methods of ligating DNA molecules will be apparent to one skilled in the art.

Vectors can be plasmids, viral-derived nucleic acids, lytic bacteriophage derived from phage lambda (λ), cosmids or filamentous single-stranded bacteriophages such as M13. Depending upon the type of host cell into which the vector is introduced, vectors are termed bacterial or eukaryotic. Bacterial vectors are derived from many sources including the genomes of plasmids and phage. Eukaryotic vectors are also constructed from a number of different sources, e.g. yeast plasmids and viruses. Some vectors, called shuttle vectors, are capable of replicating in both bacteria and eukaryotes. The nucleic acid from which the vector is derived is usually greatly reduced in size so that only those genes essential for its autonomous replication remain. The reduction in size enables the vectors to accommodate large segments of foreign DNA.

Examples of suitable vectors into which the nucleic acid encoding *Rhodococcus* phenylalanine of the present invention can be inserted include but are not limited to pBR322, pUC18, pUC19, pHSV-106, pJS97, pJS98, M13mp18, M13mp19, pSPORT 1, pGem, pSPORT 2, PSV.SPORT 1, pBluescript II, λZapII, λgt10, λgt11, λgt22A, and λZIPLOX. Other suitable vectors are obvious to one skilled in the art.

The vector of the present invention can exist in integrated or unintegrated form within the host cell and is capable of autonomous replication when in unintegrated form. The term "host cell" as used herein means the bacterial or eukaryotic cell into which the vector is introduced. As used herein, "introduced" is a general term indicating that one of a variety of means has been used to allow the vector to enter the intracellular environment of the host cell in such a way that it exists in stable form therein.

Vectors can be introduced into host cells by a number of techniques known to those skilled in the art, e.g. electroporation, DEAE dextran, cationic liposome fusion, protoplast fusion, DNA coated-microprojectile bombardment, and infection with recombinant replication-defective retroviruses. Other techniques will be obvious to one skilled in the art. The term "transformation" will be used herein as a general term to denote the introduction of vector into a bacterial or eukaryotic host cell. As such, it encompasses transformation of bacterial cells and transfection, transduction and related methods in eukaryotic cells.

Any one of a number of suitable bacterial or eukaryotic host cells may be transformed with the vector of the present invention. Examples of suitable host cells are known to one skilled in the art and include but are not limited to bacterial cells such as *E.coli* strains c600, c600hfl, HB101, LE392, Y1090, JM103, JM109, JM101, JM107, Y1088, Y1089, Y1090, Y1090(ZZ), DM1, PH10B, DH11S, DH125, RR1, TB1 and SURE, *Bacillus subtilis, Agrobacterium tumefaciens, Bacillus megaterium;* and eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator,* cultured insect cells, cultured chicken fibroblasts, cultured hamster cells, cultured human cells such as HT1080, MCF7, 143B and cultured mouse cells such as EL4 and NIH3T3 cells.

Some bacterial and eukaryotic vectors have been engineered so that they are capable of expressing inserted nucleic acids to high levels within the host cell. Such vectors utilize one of a number of powerful promoters to direct the high level of expression. For example, in vectors for the expression of a gene in a bacterial host cell such as *E.coli,* the lac operator-promoter or the tac promoter are often used. Eukaryotic vectors use promoter-enhancer sequences of viral genes, especially those of tumor viruses. Expression can be controlled in both bacterial and eukaryotic cells using inducible promoters such as the lac operator-promoter in *E.coli* or metallothionine or mouse mammary tumor virus promoters in eukaryotic cells. As used herein, "expression" refers to the ability of the vector to transcribe the inserted nucleic acid into mRNA so that synthesis of the protein encoded by the inserted nucleic acid can occur.

Vectors suitable for the expression of the nucleic acid encoding *Rhodococcus* phenylalanine dehydrogenase of the present invention in a host cell are well known to one skilled in the art and include pET-3d (Novagen), pProEx-1 (Life Technologies), pFastBac 1 (Life Technologies), PSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVl1392 (Invitrogen), pCDM8 (Invitrogen), pcDNA I (Invitrogen), pcDNA I(amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors would be apparent to one skilled in the art.

The present invention also provides a method of growing a host cell transformed with a vector encoding *Rhodococcus* L-phenylalanine dehydrogenase and recovering the recombinant L-phenylalanine dehydrogenase. As used herein the term "recombinant" refers to L-phenylalanine dehydrogenase produced by purification from a host cell transformed with a vector capable of directing the enzyme's expression to a high level. A variety of methods of growing host cells transformed with a vector are known to those skilled in the art. The type of host cell, i.e. whether the host cell is bacterial or eukaryote, is the primary determinant of the method to be utilized and the optimization of specific parameters relating to such factors as temperature, trace nutrients, humidity, and growth time. Depending on the vector, the host cells may have to be induced by the addition of a specific compound at a certain point in their growth cycle in order to initiate expression of the nucleic acid of the present invention. Examples of compounds used to induce expression of the nucleic acid of the present invention are known to one skilled in the art and include but are not limited to IPTG, zinc and dexamethasone.

Isolation and purification of recombinant *Rhodococcus* L-phenylalanine dehydrogenase can be accomplished by a number of techniques known to one skilled in the art. Such techniques usually involve growing the host cells in culture, pelleting the host cells and then lysing them by lysis methods known in the art such as treatment with lysozyme, alkali, detergent, sonication or a combination. Eukaryotic host cells can be lysed using guanidinium, detergents such as SDS or NP40, boiling with detergent, or homogenization in a Dounce homogenizer.

Cellular DNA is extracted from the host cell lysate by methods known to those skilled in the art such as precipitation with protamine sulfate. Protein is extracted by standard methods known to those skilled in the art such as ammonium sulfate precipitation followed by dialysis to remove salt. Total cellular protein is fractionated according to size, charge of the protein at specific pH values, affinity methods, or methods involving the interaction of the protein with other support matrices and the fractions analyzed by SDS-polyacrylamide gel electrophoresis. The fractions containing protein bands corresponding to the correct molecular weight are pooled.

Using standard methods of enzyme isolation and purification, active recombinant *Rhodococcus* L-phenylalanine dehydrogenase is extracted from suitable host cells transformed with vector capable of expressing the nucleic acid encoding *Rhodococcus* phenylalanine dehydrogenase of the present invention.

Active recombinant *Rhodococcus* L-phenylalanine dehydrogenase, expressed and purified from a host cell transformed with the vector of the present invention can be used in industrial processes well known in the art for the production of L-amino acids. For example, α-ketocarboxylic acid, NADH and ammonium ion can be mixed with recombinant *Rhodococcus* L-phenylalanine dehydrogenase to form the L-amino acid corresponding to the α-ketocarboxylic acid. In the example, addition of phenylpyruvic acid would produce L-phenylalanine.

The recombinant *Rhodococcus* L-phenylalanine dehydrogenase used in L-amino acid production need not be purified. Cultured broth containing cells, living cells, dried cell powders prepared by treating cells with acetone or ethanol, disrupted cells, and partially purified enzyme preparations, in addition to immobilized enzyme and immobilized enzyme-containing products prepared according to standard methods known to those skilled in the art may also be used in these reactions.

Active recombinant *Rhodococcus* L-phenylalanine dehydrogenase of the present invention may also be used as the source of enzyme in current enzyme-based methods for screening hyperphenylalaninemias such as phenylketonuria in newborn infants, as well as in methods for the routine measurement of serum phenylalanine levels to determine the efficacy of low phenylalanine diets used to control the adverse effects of phenylketonuria.

The present invention is described in the following Experimental Details Section which is set forth to aid in the understanding of the invention, and should not be construed to limit in any way the invention as defined in the claims which follow thereafter.

Experimental Details Section

A. Materials and Methods

Strains and Media—*Rhodococcus* sp. M4 (1), grown at 30° C. in YP medium (1% yeast extract, 1% L-phenylalanine, 2% glycerol, and 1% $K_2HPO_4$, pH 7.5), was used as the source of chromosomal DNA. *E.coli* DH5α was used as a host strain for cloning and plasmid construction. *E.coli* BL21(DE3) (Novagen) was used as a host for protein overexpression. Transformants were grown at 37° C. in standard LB medium (Difco) with or without 1.5% agar containing appropriate antibiotics (100 μg/ml ampicillin, 50 μg/ml kanamycin, or 50 μg/ml carbenicillin).

DNA Cloning, Mapping, and Sequencing—Chromosomal DNA was isolated from *Rhodococcus* sp. M4 using a protocol modified for mycobacterial DNA isolation (2) as described below. A 50-ml culture was inoculated with a single colony and allowed to grow until $A_{600}>7.0$ (approximately 48 h). This culture was heated at 80° C. for 30 min and then centrifuged. The pellet was resuspended in 10 ml TE buffer (10 mM Tris HCl, 1 mM EDTA, pH 8.0) followed by the addition of 0.5 ml of 10 mg/ml lysozyme and was incubated for 30 min at 37° C. After lysozyme treatment, 1.5 ml of 10% SDS and 120 μl of 10 mg/ml protease K were added and incubated for 10 min at 65° C. One ml of 5M NaCl and 1.5 ml of N-cetyl-N,N,N,-trimethylammonium bromide/NaCl (4.1 g of NaCl, 10 g of N-cetyl-N,N,N-trimethylammonium bromide in 100 ml of $H_2O$) were then added, mixed thoroughly, and incubated for 20 min at 65° C. The DNA was extracted by adding an equal volume of $CHCl_3$/isoamyl alcohol (24:1) and centrifuging. A viscous fluid formed at the interface of the aqueous and organic layers, and the separation was repeated to ensure the complete extraction of DNA. DNA was precipitated by adding 0.6 volume of isopropyl alcohol to the aqueous phase at −20° C. for 30 min and was collected by centrifugation, and the DNA-containing pellet was washed with 70% ethanol. After drying, the pellet was dissolved in a small volume of TE buffer, and $A_{260}/A_{280}$ was determined.

A genomic cosmid library of *Rhodococcus* sp. M4 DNA was generated by partial digestion with Sau3AI under conditions optimized to generate fragments within a 35-45-kilobase (kb) range. These were ligated to a 12-kb shuttle cosmid, pYUB18 (3), previously digested with BamHI. This cosmid library was packaged into λ phage using an in vitro packaging kit (Stratagene) that selects for fragments between 45 and 55 kb by the "headful" mechanism. The library was transformed into *E.coli* DH5α and stored at −70° C.

Plasmids were isolated using either a maxiprep procedure (4) or a midiprep procedure (5). Transformants were isolated using either a miniprep procedure (4) or a rapid small-scale procedure (6). Restriction enzymes were purchased from Promega; T4 DNA ligase and calf intestinal alkaline phosphatase were purchased from New England Biolabs Inc. Products of restriction endonuclease digestions were separated by electrophoresis on a 0.8% agarose slab gel in TAE buffer (40 mM Tris acetate, 1 mM EDTA, pH 8.4) containing 10 μg/ml ethidium bromide.

A 300-bp oligonucleotide probe used to screen for the phenylalanine dehydrogenase (pdh) gene was generated from a PCR using genomic *Rhodococcus* DNA as the template and two opposing primers designed from low codon redundancy regions of the purified protein's amino acid sequence. One oligonucleotide was designated from the amino terminal sequence of S-I-D-S-A-L-N-W-D-G-E-M- using the amino acids indicated in boldface (5'-ACC-TGG-GAC-GGG-GAG-ATG-3'). Similarly, the other oligonucleotide was constructed from a sequenced CNBr fragment, -A-E-N-I-D-K-L-S-G-N-Y (5'-CTT-GTC-GAT-GTT-CTC-GGC-3').

PCRs were carried out in a 100 μm concentration of each primer, a 10 mM concentration of each dNTP, and 2.5 units of AmpliTaq DNA polymerase (Perkin-Elmer) in a buffer of 10 mM Tris-HCl, 50 mM KCl, 1.5 mM $MgCl_2$, and 0.001% (w/v) gelatin, pH 8.3, following the manufacturer's guidelines. After overlaying each tube with 100 μl of mineral oil, the DNA was amplified for 36 cycles in a DNA Thermal Cycler (Perkin-Elmer). Each cycle consisted of a denaturation step of 1 min at 96° C., an annealing step of 90 s at 65° C., and finally an extension step of 1 min at 72° C. This procedure was modified by replacing dCTP with 15 μl of [$^{32}$P]dCTP (3000 Ci/mmol; DuPont NEN) to obtain a radioactively labeled PCR product. The PCR products were purified using Sephadex G-50 (fine) Quick-Spin columns (Boehringer Mannheim).

To identify transformants that contained the pdh gene, the E.coli library was plated out at low density onto kanamycin-containing plates and allowed to grow overnight. A colony blot was performed as described by Maniatis et al. (4) using nylon filters (ICN) and the radioactive 300-bp PCR probe. Several colonies that hybridized strongly with the radioactive probe were picked, grown in liquid medium, and replated to authenticate their hybridization by a second colony blot. Two colonies were selected from the second round of colony hybridization, and the inserted DNA was restricted with a battery of restriction enzymes and separated on an agarose gel. Southern hybridization was performed using ICN nylon membranes according to the company's protocol, using the radioactive PCR probe. A 2.5-kb band resulting from a PstI digest that hybridized with the probe was isolated on a DEAE membrane (Schleicher & Schuell) and ligated into a KSII vector (Stratagene) previously cleaved with PstI.

DNA sequence was determined using the dideoxy chain termination method described in the Sequenase Version 2.0 sequencing kit (United States Biochemical Corp.). 2'-Deoxy-7-deazaguanosine triphoshate was used exclusively to reduce compression artifacts. Oligonucleotides used to prime the sequencing reactions were synthesized on Applied Biosystems Model 380B DNA synthesizer. Sequences were determined on Long Rangergels (J. T. Baker Inc.) with multiple loadings. Gels were dried onto Whatman No. 3MM paper and exposed to Kodak XAR-5 film, and the determined nucleotide sequences were compiled together using the GCG sequence analysis software package (7).

Amino Acid Analysis—The purified enzyme (20 pmol) was lyophilized and then hydrolyzed in constantly boiling 6N HCl for 24 h in a sealed, evacuated tube. After the hydrolysate was evaporated to dryness, the residue was dissolved in 0.2M sodium citrate buffer, pH 2.2, and analyzed with a Hewlett-Packard amino acid analyzer.

Amino Acid Sequencing—The purified enzyme (8) was used directly for amino-terminal sequencing using an Applied Biosystems Model 477A Gas/Liquid-Phase Protein Sequencer. Internal fragments were obtained by CNBr cleavage in 80% formic acid. Peptide fragments were separated on a reverse-phase $C_8$ column using a 0.1% trifluoroacetic acid/$H_2O$, 0.1% trifluoroacetic acid/$CH_3CN$ gradient. One peptide was well separated from all others and was sequenced as described above. The purified enzyme was also digested using L-1-tosylamido-2-phenylethyl chloromethyl ketone-treated trypsin (20:1 protein/trypsin; Worthington) for 24 h. The tryptic peptides were separated on a reverse-phase $C_8$ column, and one well-resolved peak was sequenced.

Electrospray Mass Spectrometry—100 pmol of purified protein were analyzed in an API III triple quadrapole mass spectrometer (PE SCIEX), which measures charge-to-mass ratios of ionized protein molecules. The date were deconvoluted by computer to determine the protein subunit molecular mass.

Computer Search for Sequence Similarities—The GCG package (7) was used to search for similar sequences in the GenBank, EMBL, and SwissPROT data bases using the program TFASTA. This software was also used for sequence homology comparisons using the programs GAP and PILEUP.

Expression of pdh Gene—An overexpression plasmid was constructed using the pET-3d vector (Novagen), which has strong bacteriophage T7 transcription and translation signals. The pdh gene was cloned into this vector by cleaving pKSII-1B with BspHI and BamHI and isolating a 2.3-kb fragment with a DEAE membrane. The fragment was ligated to pET-3d previously cleaved with NcoI and BamHI, taking advantage of the identical overhang sequence that BspHI and NcoI share. The construct, pBL-1B, was transformed into E.coli BL21(DE3), which includes a lysogen in its genome containing a gene for T7 RNA polymerase under lacUV5 control and whose expression can be induced by the addition of isopropyl-β-D-thiogalactopyranoside (IPTG). Transformed cells were grown in LB medium to $A_{600}$=1.0, induced with 1 mM (final concentration) IPTG, and then grown for an additional 3 h. After induction, cells were lysed by lysozyme treatment followed by sonication, and the soluble cellular protein was analyzed by SDS-PAGE and activity measured.

B. Results

Cloning of Rhodococcus sp. M4 L-Phenylalanine Dehydrogenase Gene—The pdh gene was identified in a Rhodococcus genomic cosmid library using a 300-bp probe generated in a PCR using primers designed from the purified protein amino acid sequence. A cosmid containing the gene was restricted with PstI to yield a 2.5-kb fragment that hybridized with the 300-bp probe. This fragment was subcloned into the unique PstI site in the KSII vector, creating pKSII-1B, which was used for subsequent restriction mapping and sequencing (FIG. 1).

Figure 2:
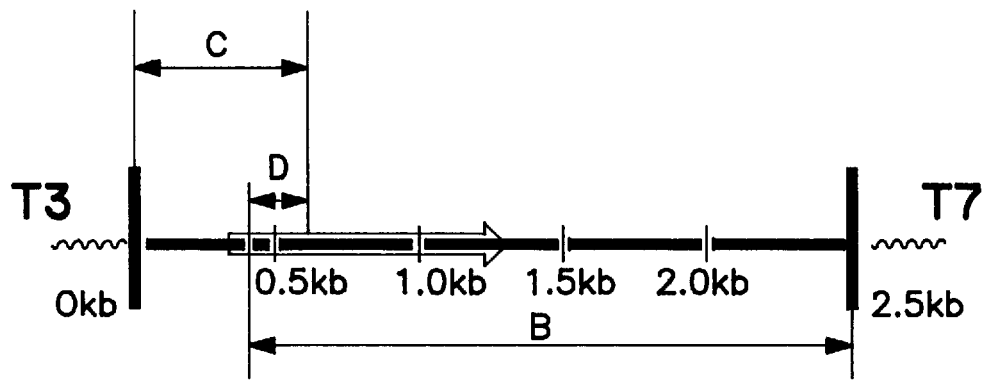
FIG. 2 depicts the orientation of the pdh gene within PKSII-1B. PCR was used with different combinations of primers to generate fragments of varied lengths, which, when arranged together resulted in the model shown. Primer combinations used were: A, amino-terminal primer+T3=no fragment; B, amino-terminal primer+T7= 2.2-kb fragment; C, internal primer+T3=0.6-kb fragment; D, amino-terminal primer+internal primer=0.3 kb-fragment (i.e. the 300 bp probe). The gene length was estimated to be approx. 1.1 kb based on the protein's subunit molecular mass of 39,500 Da and 110 Da/amino acid.

To determine the orientation and position of the pdh gene within the insert, PCR was used with the T3 and T7 primers in conjunction with the oligonucleotide primers designed from the amino acid sequences. FIG. 2 shows the gene's position, its estimated 1.1-kb length (estimated by amino acid analysis and monomer molecular mass; see below), and its orientation in the PstI fragment, suggesting that this fragment contained the entire pdh gene.

Amino Acid Composition—The amino acid composition of phenylalanine dehydrogenase was quantitated via acid cleavage of the enzyme. The amino acid composition of the enzyme was adjusted for the subunit molecular mass of approximately 39,500 Da. The cysteine and tryptophan content of the protein was not determined. The amino acid composition of the homogeneous enzyme matched well with that predicted from the nucleotide sequence (data not shown).

DNA Seauence of L-Phenylalanine Dehydrogenase Gene—The entire nucleotide sequence of the pdh gene was determined for both strands. Primers were designed initially based on the sequence of the subcloned PCR probe. Subsequent sequence was obtained by generating new primers based on the previously determined sequence.

An open reading frame of 1068 nucleotides was identified starting with an ATG codon and ending with two consecutive nonsense codons, TAG and TAA (FIG. 3). A putative, purine-rich ribosome-binding site was identified 7 bp upstream from the initiator codon. The first 37 predicted amino acids matched well with the amino-terminal sequence of the protein, determined using automated Edman degradation. The only notable difference was that the initiator methionine was not observed in the first cycle of the amino-terminal amino acid sequence. The sequence of the first 39 amino acids of the CNBr fragment ($Gly^{76}$-$Tyr^{114}$) matched the derived amino acid sequence with five exceptions, which are presumably due to misassignments of the peptide sequence. It should be noted that the sequence of this CNBr fragment begins immediately carboxyl-terminal to a predicted methionine residue, as is expected. Finally, the 13-amino acid peptide isolated from a tryptic digest matched the predicted sequence ($Glu^{300}$-$Arg^{312}$) in the carboxyl-terminal region of the protein exactly. The sequence is flanked by arginine residues, as expected for a peptide obtained by tryptic digestion.

The deduced sequence of 356 amino acids corresponds to a subunit molecular mass of 36,609 Da, which agrees with the apparent subunit molecular mass of 39,500 Da determined by SDS-PAGE analysis (8). Electrospray mass spectrometry was used to determine a protein molecular mass of 36,484 Da±10 Da (data not shown; this corresponds to the mass of the full length enzyme minus the amino terminal methionine residue (36,609−132=36,477). Table I compares codon usage for the *Rhodococcus* pdh gene and the reported codon usage for mycobacterial phage L5 (9). The codon usage is very similar, with the third base position in each codon uniformly preferring cytidine or guanosine over thymidine or adenosine. This observation suggests the possibility of using mycobacterial codon bias as a guide for the design of minimally redundant oligonucleotide probes for genes of *Rhodococcus*. The pdh gene has a 65% G+C content, which is typical for the *Rhodococcus* genus (10).

Comparison of Amino Acid Sequence with Those of Other Amino Acid Dehydrogenases—The GAP program from the GCG package (7) was used for alignments between representative amino acid dehydrogenases, with gaps introduced to maximize identities. Table II displays the results of these comparisons. The highest homology was found between *Rhodococcus* phenylalanine dehydrogenase and the leucine dehydrogenase from *B.stearothermophilus*, followed by the phenylalanine dehydrogenases from *B.sphaericus* and *T.intermedius*. Regions of homology in these cases were uniformly distributed throughout the protein sequence.

A close examination of the regions of homology reveals residues that are particularly well conserved for both the leucine and phenylalanine dehydrogenases from all species. FIG. 4 shows a comparison of amino acid dehydrogenases in the carboxyl-terminal nucleotide-binding domain. This region in the x-ray crystallographically determined structure of *Clostridium symbiosum* glutamate dehydrogenase (11) can be identified with residues in the βG-α10-βH region. These secondary structural elements represent the initial half of the Rossmann fold, which consists of a β-α-β-β-α-α-β-β-α-β structure. The asterisks in FIG. 4 highlight the locations of conserved residues in the dinucleotide-binding domain (12). There are additional residues that are conserved within the amino acid dehydrogenase family, but not within other dehydrogenases (i.e. malate, lactate, and alcohol dehydrogenases), including Arg/$Leu^{177}$, $Gly^{199}$, and Ala/$Gly^{200}$. All residue numbering in the following discussion refers to the numbering of the *Rhodococcus* pdh gene.

A second region of high homology exists between amino acid dehydrogenases, which is thought to be the amino acid-binding and catalytic domain of these enzymes (13). FIG. 5 shows an alignment of several amino acid dehydrogenases with secondary structure predictions again based on the determined three-dimensional structure of *C.symbiosum* glutamate dehydrogenase (11). The most dramatic finding is the complete lack of homology in this region between alanine dehydrogenases and the other amino acid dehydrogenases, whereas a high degree of homology exists in this region among the other amino acid dehydrogenases. Glutamate, leucine, and phenylalanine dehydrogenases can be separated into two groups based on significant homology within each group, but not between them. As shown by the boxed residues, these groups include the glutamate dehydrogenases and the phenylalanine and leucine dehydrogenases.

Figure 6:
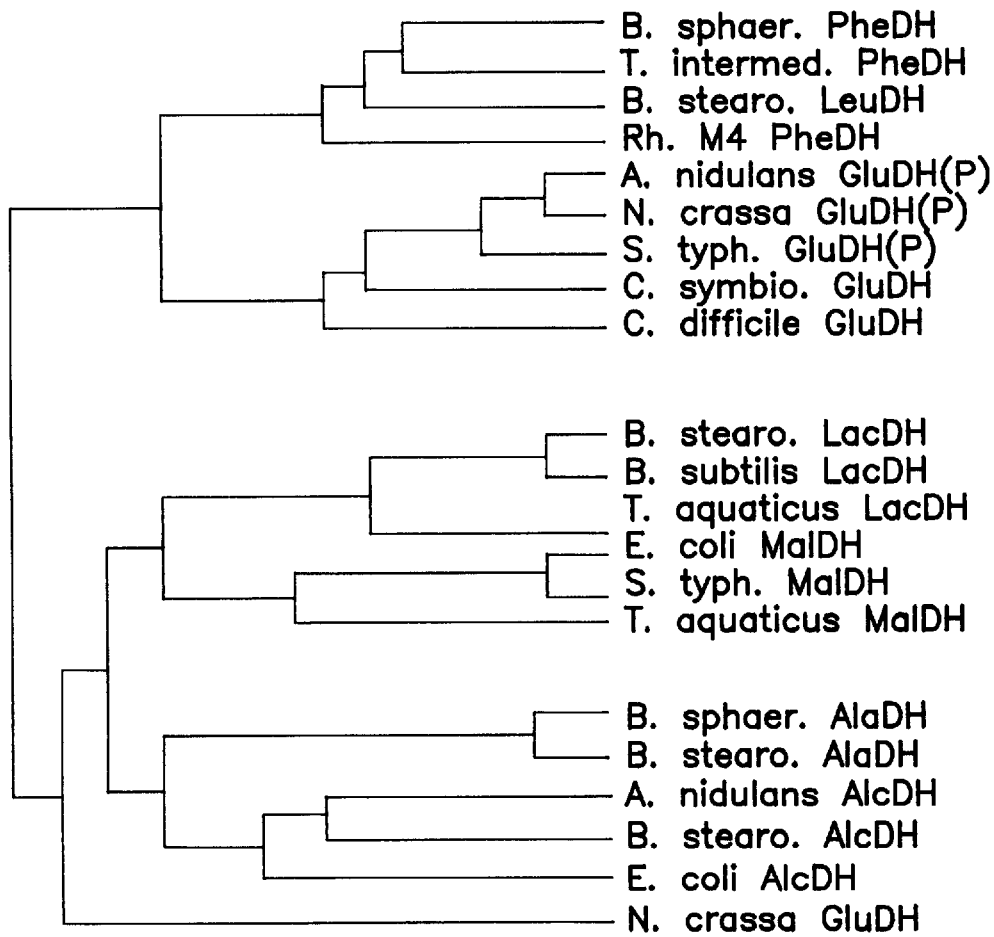
FIG. 6 depicts a dendogram based on degree of sequence similarity between a variety of dehydrogenases, generated by program PILEUP (7). The enzymes listed in this tree are as follows: *B.sphaericus* phenylalanine dehydrogenase (PheDH), *T.intermedius* phenylalanine dehydrogenase (PheDH), *B.stearothermophilus* leucine dehydrogenase (LeuDH), *Rhodococcus* sp. M4 phenylalanine dehydrogenase, *Aspergillus nidulans* NADP-dependent glutamate dehydrogenase (GluDH(P)) (14), *N.crassa* NADP-dependent glutamate dehydrogenase (15), *Salmonella typhimurium* NADP-dependent glutamate dehydrogenase (16), *C.symbiosum* glutamate dehydrogenase (GluDH), *C.difficile* glutamate dehydrogenase, *B.stearothermophilus* lactate dehydrogenase (LacDH) (17), *Bacillus subtilis* lactate dehydrogenase (18), *Thermus aguaticus* lactate dehydrogenase (19), *E.coli* malate dehydrogenase (MalDH) (20), *S.typhimurium* malate dehydrogenase (Lu, C. D., and Abdelal, A. T. (1991) GenBank™/EMBL/DDBJ accession number M95049), *T.aquaticus* malate dehydrogenase (21), *B.sphaericus* alanine dehydrogenase (AlaDH), *B.stearothermophilus* alanine dehydrogenase, *A.nidulans* alcohol dehydrogenase (AlcDH) (22), *B.stearothermophilus* alcohol dehydrogenase (23), *E.coli* alcohol dehydrogenase (24), and *N.crassa* glutamate dehydrogenase (25). References are as listed in the legend to FIG. 4 unless noted.

Evolutionary Lineage of Amino Acid Dehydrogenases— To assess the possible evolutionary relationships between the amino acid dehydrogenases, the amino acid sequences of a number of each enzyme type were compared with a sample of primary and secondary alcohol dehydrogenases; lactate, malate, and alcohol dehydrogenases. FIG. 6 represents a dendrogram, which groups together the enzymes based on their degree of sequence relatedness. The leucine and phenylalanine dehydrogenases form one distinct group, the glutamate dehydrogenases form another, and the lactate and malate dehydrogenases form their own cluster. Alanine dehydrogenases cluster very distantly from the other amino acid dehydrogenases and form a group within the alcohol dehydrogenase family.

Expression of pdh Gene—Upon induction, the BL-1B cells overproduced a protein that had the same electrophoretic mobility on SDS-PAGE as authentic L-phenylalanine dehydrogenase isolated from *Rhodococcus* sp. M4. From time course studies, 3 h of induction maximized enzyme expression (data not shown).

Cell-free extracts of induced *E.coli* BL-1B cells were shown to have phenylalanine dehydrogenase activity, which is absent in nontransformed *E.coli* BL21(DE3) cells. Expressed *Rhodococcus* phenylalanine dehydrogenase was purified from BL-1B cells and exhibited identical activity and physical properties to the enzyme purified from *Rhodococcus*. The purified expressed enzyme exhibited a monomer molecular mass of 36,481 Da±10 Da, determined by electrospray mass spectroscopy, similar to the mass of 36,484 Da±10 Da determined for the enzyme purified from *Rhodococcus*. In addition, the first 10 amino acids of the purified expressed protein were sequenced by Edman degradation and matched the amino-terminal sequence from *Rhodococcus*.

References

1. Hummel, W., Schutte, H., Schmidt, E., Wandrey, C., and Kula, M.-R. (1987) *Appl. Microbiol. Biotechnol.* 26: 409–416.

2. van Soolingen, D., Hermans, P. W. M., DeHaas, P. E. W., Soll, D. R., and van Embden, J. D. A. (1991) *J. Clin. Microbiol.* 29: 2578–2586.

3. Snapper, S. B., Melton, R. E., Mustafa, S., Kieser, T., and Jacobs, W. R.,Jr. (1990) *Mol. Microbiol.* 4: 1911–1919.

4. Maniatis, T., Fritsch, E. F., and Sambrook, J. (1982) *Molecular Cloning: A Laboratory Manual*, Cold Spring Harbor Laboratory, Cold Spring Harbor, N.Y.

5. Liszewski, M. K., Kumar, V., and Atkinson, J. P. (1989) *BioTechniques* 7: 1079–1081.

6. Serghini, M. A., Ritzenthaler, C., and Pinck, L. (1989) *Nucleic Acids Res.* 17: 3604.

7. Devereux, J., Haeberli, P., and Smithies, O. (1984) *Nucleic Acids Res.* 12: 387–395.

8. Brunhuber, N. M. W., and Blanchard, J. S. (1993) *FASEB* 7: 1069 (abst.).

9. Hatfull, G. F., and Sarkis, G. J. (1993) *Mol. Microbiol.* 7: 395–405.

10. Finnerty, W. R. (1992) *Ann. Rev. Microbiol.* 46: 193–218.

11. Baker, P. J., Britton, K. L., Engel, P. C., Farrants, G. W., Lilley, K. S., Rice, D. W., and Stillman, T. J. (1992) *Proteins Struct. Funct. Genet.* 12: 75–86.

12. Branden, C., and Tooze, J. (1991) Introduction to Protein Structure, Garland Publishing, Inc., New York.

13. Kuroda, S., Tanizawa, K., Sakamoto, Y., Tanaka, H., and Soda, K. (1990) *Biochemistry* 29: 1009–1015.

14. Hawkins, A. R., Gurr, S. J., Montague, P., and Kinghorn, J. R. (1989) *Mol. Gen. Genet.* 218: 105–111.

15. Kinnaird, J. H., and Fincham, J. R. S. (1983) *Gene* (Amst.) 26: 253–260.

16. Bansal, A., Dayton, M. A., Zalkin, H., and Colman, R. F. (1989) *J. Biol. Chem.* 264: 9827–9835.

17. Barstow, D. A., Clarke, A. R., Chia, W. N., Wigley, D., Sharman, A. F., Holbrook, J. J., Atkinson, J., and Minton, N. P. (1986) *Gene* (Amst.) 46: 47–55.

18. Hediger, M. A., Frank, G., and Zuber, H. (1986) *Biol. Chem. Hoppe-Seyler* 367: 891–903.

19. Ond, M., Matsuzawa, H., and Ohta, T. (1990) *J. Biochem.* (Tokyo) 107: 21–26.

20. McAlister-Henn, L., Blaber, M., Bradshaw, R. A., and Nisco, S. J. (1987) *Nucleic Acids Res.* 15: 4993.

21. Nishiyama, M., Matsubara, N., Yamamoto, K., Iijima, S., Vozumi, T., and Beppu, T. (1986) *J. Biol. Chem.* 261: 14178–14183.

22. Gwynne, D. I., Buxton, F. P., Sibley, S., Davies, R. W., Lockington, R. A., Scazzocchio, C., and Sealy-Lewis, H. M. (1987) *Gene* (Amst.) 51: 205–216.

23. Bridgen, J., Kolb, E., and Harris, J. I. (1987) *FEBS Lett.* 33: 1–3.

24. Gutheil, W. G., Holmquist, B., and Vallee, B. L. (1992) *Biochemistry* 31: 475–481.

25. Haberland, M. E., and Smith, E. L. (1980) *J. Biol. Chem.* 255: 7984–7992.

26. Nagata, S., Tanizawa, K., Esaki, N., Sakamoto, Y., Ohshima, T., Tanaka, H., and Soda, K. (1988) *Biochemistry* 27: 9056–9062.

27. Okazaki, N., Hibino, Y., Asano, Y., Ohmori, M., Numao, N., and Kondo, K. (1988) *Gene* (Amst.) 63: 337–376.

28. Takada, H., Yoshimura, T., Ohshima, T., Esaki, N., and Soda, K. (1991) *J. Biochem.* (Tokyo) 109: 371–376.

29. Lilley, K. S., Baker, P. J., Bitton, K. L., Stillman, T. J., Brown, P. E., Moir, A. J. G., Engel, P. C., Rice, D. W., Bell, J. E., and Bell, E. (1991) *Biochem. Biophys. Acta.* 1080: 191–197.

All publications mentioned hereinabove are hereby incorporated in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

TABLE 1

L-Phenylalanine Dehydrogenase Sequence
Comparison of codon usage for *Rhodococcus sp.* M4 pdh gene and mycobacterial phage L5
Mycobacterial phage L5 usage was as predicted by Hatfull and Sarkis (9)

| Amino Acid | Codon | pdh usage | Mycobacterial usage | Amino Acid | Codon | pdh usage | Mycobacterial usage |
|---|---|---|---|---|---|---|---|
| Gly | GGG | 0.14 | 0.16 | Trp | TGG | 1.00 | 1.00 |
| Gly | GGA | 0.24 | 0.14 | End | TGA | 0.00 | 0.67 |
| Gly | GGT | 0.19 | 0.19 | Cys | TGT | 0.67 | 0.22 |
| Gly | GGC | 0.43 | 0.51 | Cys | TGC | 0.33 | 0.78 |
| Glu | GAG | 0.76 | 0.79 | End | TAG | 0.00 | 0.14 |
| Glu | GAA | 0.24 | 0.21 | End | TAA | 0.00 | 0.19 |
| Asp | GAT | 0.16 | 0.19 | Tyr | TAT | 0.00 | 0.08 |
| Asp | GAC | 0.84 | 0.81 | Tyr | TAC | 1.00 | 0.92 |
| Val | GTG | 0.23 | 0.30 | Leu | TTG | 0.19 | 0.10 |
| Val | GTA | 0.06 | 0.07 | Leu | TTA | 0.00 | 0.00 |
| Val | GTT | 0.23 | 0.09 | Phe | TTT | 0.00 | 0.05 |
| Val | GTC | 0.48 | 0.54 | Phe | TTC | 1.00 | 0.95 |
| Ala | GCG | 0.31 | 0.30 | Ser | TCG | 0.35 | 0.35 |
| Ala | GCA | 0.21 | 0.13 | Ser | TCA | 0.13 | 0.07 |
| Ala | GCT | 0.05 | 0.19 | Ser | TCT | 0.00 | 0.07 |
| Ala | GCC | 0.43 | 0.38 | Ser | TCC | 0.30 | 0.22 |
| Arg | AGG | 0.00 | 0.09 | Arg | CGG | 0.21 | 0.27 |
| Arg | AGA | 0.05 | 0.03 | Arg | CGA | 0.32 | 0.18 |
| Ser | AGT | 0.04 | 0.03 | Arg | CGT | 0.11 | 0.10 |
| Ser | AGC | 0.17 | 0.25 | Arg | CGC | 0.32 | 0.33 |
| Lys | AAG | 0.60 | 0.92 | Gln | CAG | 0.50 | 0.88 |
| Lys | AAA | 0.40 | 0.08 | Gln | CAA | 0.50 | 0.12 |
| Asn | AAT | 0.17 | 0.08 | His | CAT | 0.22 | 0.13 |
| Asn | AAC | 0.83 | 0.92 | His | CAC | 0.78 | 0.87 |
| Met | ATG | 1.00 | 1.00 | Leu | CTG | 0.38 | 0.46 |
| Ile | ATA | 0.07 | 0.03 | Leu | CTA | 0.00 | 0.05 |
| Ile | ATT | 0.21 | 0.06 | Leu | CTT | 0.06 | 0.06 |
| Ile | ATC | 0.71 | 0.91 | Leu | CTC | 0.38 | 0.33 |
| Thr | ACG | 0.16 | 0.29 | Pro | CCG | 0.70 | 0.51 |
| Thr | ACA | 0.13 | 0.07 | Pro | CCA | 0.00 | 0.10 |
| Thr | ACT | 0.13 | 0.08 | Pro | CCT | 0.10 | 0.11 |
| Thr | ACC | 0.58 | 0.56 | Pro | CCC | 0.20 | 0.28 |

TABLE II

Percent sequence identity of *Rhodococcus sp.* M4 pdh gene to other amino-acid dehydrogenases
Sequences were compared to each other using the program GAP (7). Specific references are as follows:
phenylalanine dehydrogenase, (PheDH), *Rhodoccus sp.* M4; Leucine dehydrogenase (LeuDH),
*B. stearothermophilus* (26); phenylalanie dehydrogenase, *B. sphaericus* (27);
phenylalanine dehydrogenase, *T. intermedius* (28); glutamate dehydrogenase (GluDH), *C. difficile*
(Lyerly, D.M., Barroso, L.A., and Wilkins, T.D. (1991) GenBank ™ /EMBL/DDBJ accession number
M65250); glutamte dehydrogenase, *C. symbiosum* (29); alanine dehydrogenase (AlaDH),
*B. stearothermophilus* (13); alanine dehydrogenase, *B. sphaericus* (13).

| Protein | LeuDH, B. stearothermophilus | PheDH, B. sphaericus | PheDH, T. intermedius | GLuDH, C. difficule |
|---|---|---|---|---|
| PheDH, Rhodococcus M4 | 38.9 | 34.0 | 32.0 | 25.8 |
| LeuDH, B. stearothermophilus | | 51.8 | 47.1 | 28.5 |
| PheDH, B. sphaericus | | | 53.4 | 26.1 |
| PheDH, T. intermedius | | | | 28.4 |
| GLuDH, C. difficile | | | | |
| GLuDH, C. symbiosum | | | | |
| ALaDH, B. stearothermophilus | | | | |

| Protein | GLuDH, C. symbiosum | ALaDH, B. stearothermophilus | ALaDH, B. sphaericus |
|---|---|---|---|
| PheDH, Rhodococcus M4 | 17.7 | 17.6 | 17.9 |
| LeuDH, B. stearothermophilus | 19.7 | 20.4 | 16.1 |
| PheDH, B. sphaericus | 19.0 | 16.3 | 21.6 |
| PheDH, T. intermedius | 17.3 | 22.8 | 18.8 |
| GLuDH, C. difficile | 25.1 | 16.0 | 13.4 |
| GLuDH, C. symbiosum | | 19.9 | 18.9 |
| ALaDH, B. stearothermophilus | | | 73.2 |

---

What is claimed is:

1. A purified and isolated nucleic acid encoding *Rhodococcus* L-phenylalanine dehydrogenase.

2. The nucleic acid of claim 1 which encodes the amino acid sequence set forth in SEQ ID NO: 2 and shown in FIG. 3.

3. The nucleic acid of claim 1 having the nucleotide sequence set forth in SEQ ID NO: 1 and shown in FIG. 3.

4. A vector comprising nucleic acid encoding *Rhodococcus* L-phenylalanine dehydrogenase.

5. The vector of claim 4, wherein the nucleic acid encodes the amino acid sequence set forth in SEQ ID NO: 2 and shown in FIG. 3.

6. The vector of claim 4, wherein the nucleic acid has the nucleotide sequence set forth in SEQ ID NO: 1 and shown in FIG. 3.

7. A host cell transformed by a vector comprising nucleic acid encoding *Rhodococcus* L-phenylalanine dehydrogenase.

8. The host cell of claim 7, wherein the nucleic acid encodes the amino acid sequence set forth in SEQ ID NO: 2 and shown in FIG. 3.

9. The host cell of claim 7, wherein the vector comprises the nucleic acid having the nucleotide sequence set forth in SEQ ID NO: 1 and shown in FIG. 3.

10. The host cell of claim 7, wherein the host cell is *E.coli*.

11. A method for producing recombinant *Rhodococcus* L-phenylalanine dehydrogenase comprising growing a host cell transformed with a vector comprising nucleic acid encoding *Rhodococcus* L-phenylalanine dehydrogenase in culture, and recovering L-phenylalanine dehydrogenase from the culture.

12. The method of claim 11, wherein the nucleic acid encodes the amino acid sequence set forth in SEQ ID NO: 2 and shown in FIG. 3.

13. The method of claim 11, wherein the nucleic acid has the nucleotide sequence set forth in SEQ ID NO: 1 and shown in FIG. 3.

14. The method of claim 11, wherein the host cell is *E.coli*.

* * * * *